US006221616B1

(12) United States Patent
Salon et al.

(10) Patent No.: US 6,221,616 B1
(45) Date of Patent: Apr. 24, 2001

(54) DNA ENCODING A HUMAN MELANIN CONCENTRATING HORMONE RECEPTOR (MCH1) AND USES THEREOF

(75) Inventors: John A. Salon, Montclair; Thomas M. Laz, Parlin; Raisa Nagorny, Fair Lawn, all of NJ (US); Amy E. Wilson, New York, NY (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/478,601

(22) Filed: Jan. 6, 2000

Related U.S. Application Data

(62) Division of application No. 09/224,426, filed on Dec. 31, 1998.

(51) Int. Cl.⁷ .................................................. G01N 33/53
(52) U.S. Cl. .......................... 435/7.1; 536/23.5; 530/350; 435/325; 435/348; 435/357; 435/361; 435/356; 435/365; 435/366; 435/372
(58) Field of Search .................. 530/350; 536/23.5; 435/7.1, 7.2, 252.3, 361, 320.1, 7.21, 336, 348, 357, 365, 366

(56) References Cited

FOREIGN PATENT DOCUMENTS

| | | |
|---|---|---|
| 0848060 | 6/1998 | (EP) . |
| 9618651 | 6/1996 | (WO) . |
| 9639162 | 12/1996 | (WO) . |
| 9928492 | 6/1999 | (WO) . |

OTHER PUBLICATIONS

Expressed Sequence Tags Database Accession No. F 07228 (Published Feb. 15,1995).
Expressed Sequence Tags Database Accession No. HSU 71092 (Published Dec. 21, 1996).
Expressed Sequence Tags Database Accession No. AF 008650 (Published Oct. 1, 1997).
Expressed Sequence Tags Database Accession No. Z 86090 (Published Feb. 22, 1997).
Expressed Sequence Tags Database Accession No. T 30384 (Published Sep. 13, 1996).
Expressed Sequence Tags Database Accession No. V 28115 (Published Sep. 25, 1998).
Auffray, C., et al. IMAGE: intégration au niveau moléculaire de l ' analyse du génome humain et de son expression. *C.R. Acad. Sci. Paris, Sci. Vie* (1995) 318: 263–272.
Kolakowski, L.F., et al. Characterization of a human gene related to genes encoding somatostatin receptors. *FEBS Letters* (1996) 398: 253–258.
Lakaye, B., et al. Cloning of the rat brain cDNA encoding for the SLC–1 G protein–coupled reveals the presence of an intron in the gene. *Biochimica et Biophysica Acta* (Feb. 4, 1998) 1401 (2) : 216–220 ; and.
Shimada, M., et al. Mice lacking melanin–concentrating hormone are hypophagic and lean. *Nature* (Dec. 17, 1998) 396: 670–674.

*Primary Examiner*—Lorraine Spector
*Assistant Examiner*—Eileen B. O'Hara
(74) *Attorney, Agent, or Firm*—John P. White; Cooper & Dunham LLP

(57) ABSTRACT

This invention provides an isolated nucleic acid encoding a human MCH1 receptor, a purified human MCH1 receptor, vectors comprising isolated nucleic acid encoding a human MCH1 receptor, cells comprising such vectors, antibodies directed to a human MCH1 receptor, nucleic acid probes useful for detecting nucleic acid encoding human MCH1 receptors, antisense oligonucleotides complementary to unique sequences of nucleic acid encoding human MCH1 receptors, transgenic, nonhuman animals which express DNA encoding a normal or mutant human MCH1 receptor, methods of isolating a human MCH1 receptor, methods of treating an abnormality that is linked to the activity of a human MCH1 receptor, as well as methods of determining binding of compounds to mammalian MCH1 receptors.

8 Claims, 11 Drawing Sheets

FIGURE 1

```
   1 ATGTCAGTGGGAGCCATGAAGAAGGGAGTGGGGAGGCAGTTGGGCTTGGAGGCGGCAGC      60
  61 GGCTGCCAGGCTACGGAGGAAGACCCCCTTCCCGACTGCGGGGCTTGCGCTCCGGGACAA     120
 121 GGTGGCAGGCGCTGGAGGCTGCCGCCTGCGTGGGTGGAGGGAGCTCAGCTGCTCGGTTG     180
 181 TGGGAGCAGGCGACCGGCCACTGGCTGGATGGACCTGGAAGCCTCGCTGCTGCCCACTGGT    240
 241 CCCAATGCCAGCAACACCTCTGATGGCCCCGATAACCTCACTTCAGCAGGATCACCTCCT    300
 301 CGCACGGGGAGCATCTCTACATCATCATGCCTTCGGTGTTCGGCACCATCTGC           360
 361 CTCCTGGGCATCGGGAACTCCACGGTCATCTTCATCATTCGCGGTCGTGAAGAAGTCCAAGCTG   420
 421 CACTGGTGCAACAACGTCCCCGACATCTTCATCATCCACCAGCTCATGGGCAATGGGGTGTGGCACTTT   480
 481 TTTCTCCTGGGCATGCCACCCGCCATGCCCCTCATCACGGCCATGTGACCGCCACTGGCCACCAGCACC   540
 541 GGGGAGACCATGTGCACCCGGAAGCCCTCTGTGGCTGTGCTGCCAATAGTCAGTTCAGCAGCACC     600
 601 TACATCCTGACCGCCATCACCCCTGGCCACCTGACCCATCCGGTGATCGTCCACCCCATCTCTCC     660
 661 ACGAAGTTCCGGACATCAGCATCATCACCCTGGTATGCCAGACACTGACCTCATCACCTGTTCACCCTGTAC    720
 721 TTCATCAGCATCATCACGCTGCCCAAACCCAGACGCCTTTGTGCCCTTGGTCATCACACGCCGCATACGTGAGGATC   780
 781 GTGGGCTGCGGCATGACCCGCACAGTTCCTCAGTGGCCTCCAGTGCCCTCCCCAGCGCAGCATCCGGCTGCCGGACA   840
 841 CAGTTTTCCTGGCCCTTTGCCCTGCCCCTTGTGCCCCCGCCATCTGTGGTCTTCTTGTGCTGGGCACCC     900
 901 CTGCAGCGCATGACGTCCTCAGTGGCCCACAGCCATGTCCATCAGCCGCCGACCCTCACCTTTGTCTAC     960
 961 AAGAGGGTGACCCGCACAGCTGACCCAGTTGTCCATCAGCCGCCCGACCCTCACCTTTGTCTAC           1020
1021 TACTATGTGCTACAGCGGCCATCAGCTTGGGCTTCCGCAAACGCTTCCTGTGAAGCCTGCAGCCAG         1080
1081 TTATACAATGCCTATACAATGCCCTGAGACGTTCCGCAAACGCTTCCTGTGAAGCCTGCAGCCAG           1140
1141 ATCGTGCTCTGTGAGACGTTCCGCAAACGCTTCCTGTGAAGCCTGCAGCCAG            1200
1201 GGGCAGCTTCGCGCTGTCAGCAACGCTCAGACGCTCAGACGCTCAGACGCTCAGACGCTCAGAAAAGCAAA     1260
1261 GGCACCTGA                                                                      1269
```

```
  1  M S V G A M K K G V G R A V G L G G G S   20
 21  G C Q A T E E D P L P D C G A C A P G Q   40
 41  G G R R W R L P Q P A W V E G S S A R L   60
 61  W E Q A T G T G W M D L E A S L L P T G   80
 81  P N A S N T S D G P D N L T S A G S P P  100
101  R T G S I S Y I N L I M P S V F G T I C  120
                    I
121  L L G I I G N S T V I F A V V K K S K L  140
                                      II
141  H W C N N V P D I F I I N L S V V D L L  160
161  F L L G M P F M I H Q L M G N G V W H F  180
181  G E T M C T L I T A M D A N S Q F T S T  200
                              III
201  Y I L T A M A I D R Y L A T V H P I S S  220
221  T K F R K P S V A T L V I C L L W A L S  240
                    IV
241  F I S I T P V W L Y A R L I P F P G G A  260
261  V G C G I R L P N P D T D L Y W F T L Y  280
                                V
281  Q F F L A F A L P F V V I T A A Y V R I  300
301  L Q R M T S S V A P A S Q R S I R L R T  320
                                VI
321  K R V T R T A I A I C L V F F V C W A P  340
341  Y Y V L Q L T Q L S I S R P T L T F V Y  360
                              VII
361  L Y N A A I S L G Y A N S C L N P F V Y  380
381  I V L C E T F R K R L V L S V K P A A Q  400
401  G Q L R A V S N A Q T A D E E R T E S K  420
421  G T                                      422
```

FIGURE 4

```
   1  GCAGGCGACCTGCACCGGCTGCATGGATCTGCAAACCTCGTTGCTGTCCACTGGCCCCAA    60
  61  TGCCAGCAACATCTCCGATGGCCAGGATAATCTCACATTGCCCGGGTCACCTCCTCGCAC   120
 121  AGGGAGTGTCTCCTACATCAACATCATTATGCCTTCCGTGTTTGGTACCATCTGTCTCCT   180
 181  GGGCATCGTGGGAAACTCCACGTCATCTTTGCTGTGTGAAGAAGTCCAAGTACACACTG   240
 241  GTGCAGCAACGTCCCCGACATCTTCATCATCAACCTCTCTGTGGTGGATCTGCTCTTCCT   300
 301  GCTGGGCATGCCTTTCATGATCCACCAGCTCATGGGGAACGGCGTCTGGCACTTTGGGGA   360
 361  AACCATGTGCCACCCTCATCACAGCCATGGCCAACAGTCAGTTCACTAGCACCTACAT    420
 421  CCTGACTGCCATGACCATTGACCGCTACTTGGCCACCACCGTCCACCCATCTCCTCCACCAA   480
 481  GTTCCCGGAAGCCCCTCGTGTGGCTCTACGCCCAGGCTCATTCCTGTGGGCGCTCTCCTCAT   540
 541  CAGTATCACCCCCTGTGTGCCCTGCCAAAACCCGGACACTGACCTGTCATTACCGCCATCA   600
 601  CTGTGGCATCCGCCTTTGCCCCTTTGCCCTTTCCGTTTGTGGTCATTACCGCCATACGTGAAATACTACA   660
 661  TTTCCTGGCCTCTTTGCCCTTTCCGTTTGTGGTCATTACCGCCATACGTGAAATACTACA   720
 721  GCGCATGACGTCTTCGGTGCCCCAGCTCTCTGTGCCATTGCTCTTCTTTGCTGTGGCACCCTACTA   780
 781  GGTGACCCGCACGGCCATTGACCTGAGCTGCAGTGCCCAGTGTTTGTCTCACGTTTGTCTACTTGTA   840
 841  TGTGCTGCAGTGACCCATCAGCTTGGGCTATGCTAACAGCTGCCTGAACCCCTTTGTGTACATAGT   900
 901  CAACGCGGCCATCAGTGAGACCTTTCGAAAACGCTTGGTGTTGTCAGCCCCAGGGGCA   960
 961  GCTCCGCACGGTCAGCAACGCTCAGACAGCTGATGAGGAGGACAGAAAGCAAAGGCAC  1020
1021  CTGACAATTCCCCAGTCGCCCTCCCAAGTCAGGCCACCACCCCATCAAAACCGTGGGAGAGATAC  1080
1081  TGAGATTAAACCCAAGGCTACCCCTGGGAGAATGCAGAGGCTGGAGGCTGGGGCTTGTAG  1140
1141  CAACCACATTCCAC                                              1214
```

IP release in MCH1- and mock-transfected Cos-7 cells

FIGURE 10
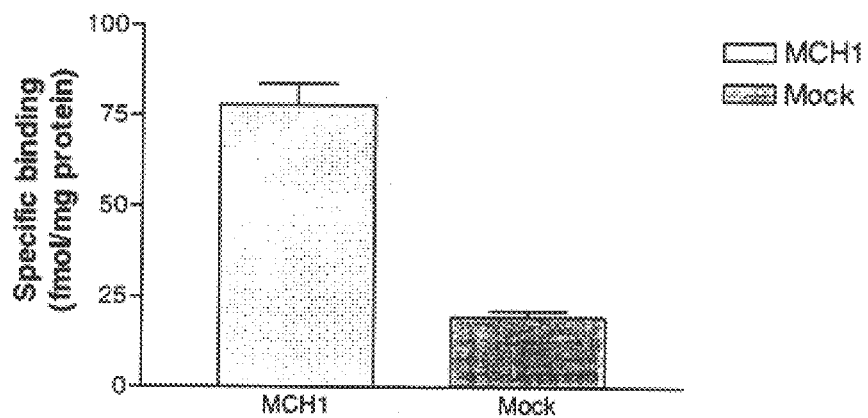

DNA ENCODING A HUMAN MELANIN CONCENTRATING HORMONE RECEPTOR (MCH1) AND USES THEREOF

This application is a divisional of U.S. Ser. No. 09/224,426, filed Dec. 31, 1998, the content of which is hereby incorporated by reference into the subject application.

BACKGROUND OF THE INVENTION

Throughout this application, various publications are referenced in parentheses by author and year. Full citations for these references may be found at the end of the specification immediately preceding the sequence listings and the claims. The disclosure of these publications in their entireties are hereby incorporated by reference into this application to describe more fully the state of the art to which this invention pertains.

Neuroregulators comprise a diverse group of natural products that subserve or modulate communication in the nervous system. They include, but are not limited to, neuropeptides, amino acids, biogenic amines, lipids and lipid metabolites, and other metabolic byproducts. Many of these neuroregulator substances interact with specific cell surface receptors which transduce signals from the outside to the inside of the cell. G-protein coupled receptors (GPCRs) represent a major class of cell surface receptors with which many neurotransmitters interact to mediate their effects. GPCRs are predicted to have seven membrane-spanning domains and are coupled to their effectors via G-proteins linking receptor activation with intracellular biochemical sequelae such as stimulation of adenylyl cyclase.

Melanin-concentrating hormone (MCH) is a cyclic peptide originally isolated from salmonid (teleost fish) pituitaries (Kawauchi et al., 1983). In fish the 17 amino acid peptide causes aggregation of melanin within the melanophores and inhibits the release of ACTH, acting as a functional antagonist of α-MSH. Mammalian MCH (19 amino acids) is highly conserved between rat, mouse, and human, exhibiting 100% amino acid identity, but its physiological roles are less clear. MCH has been reported to participate in a variety of processes including feeding, water balance, energy metabolism, general arousal/attention state, memory and cognitive functions, and psychiatric disorders (for reviews, see Baker, 1991; Baker, 1994; Nahon, 1994; Knigge et al., 1996). Its role in feeding or body weight regulation is supported by a recent Nature publication (Qu et al., 1996) demonstrating that MCH is overexpressed in the hypothalamus of ob/ob mice compared with ob/+mice, and that fasting further increased MCH mRNA in both obese and normal mice during fasting. MCH also stimulated feeding in normal rats when injected into the lateral ventricles (Rossi et al., 1997). MCH also has been reported to functionally antagonize the behavioral effects of α-MSH (Miller et al., 1993; Gonzalez et al, 1996; Sanchez et al., 1997); in addition, stress has been shown to increase POMC mRNA levels while decreasing the MCH precursor preproMCH (ppMCH) mRNA levels (Presse et al., 1992). Thus MCH may serve as an integrative neuropeptide involved in the reaction to stress, as well as in the regulation of feeding and sexual activity (Baker, 1991; Knigge et al., 1996).

The gene encoding the MCH precursor (ppMCH) has been cloned and encodes two additional peptides, neuropeptide EI (13 AA) and neuropeptide GE (19AA) (Nahon et al., 1989), which may also have biological activity. MCH peptide is synthesized primarily in hypothalamic neurons (the zona incerta and lateral hypothalamus) which project diffusely to many brain areas and to the pituitary (Bittencourt et al., 1992); NEI has also been identified in medium from explanted hypothalamic neurons (Parkes and Vale, 1993). Localization studies of the mRNA indicate that MCH is also present in the periphery (testes and GI tract; Hervieu and Nahon, 1995) but the highest concentrations are in the hypothalamus. There is also evidence for differential tissue-dependent processing of proMCH in mammals. A shorter MCH gene transcript that may result from alternate splicing was found in several brain areas and peripheral tissues, and a different peptide form was also found in the periphery (Viale et al., 1997). In humans, the gene encoding authentic MCH has been localized to chromosome 12, but two copies of a variant (truncated) gene are present on chromosome 5 (Breton et al., 1993); the functional significance, if any, of the variant is not yet known. Finally, the rat MCH gene may encode an additional putative peptide in a different reading frame (Toumaniantz et al., 1996).

Although the biological effects of MCH are believed to be mediated by specific receptors, binding sites for MCH have not been well described. A tritiated ligand ([$^3$H]-MCH) was reported to exhibit specific binding to brain membranes but was unusable for saturation analyses, so neither affinity nor $B_{max}$ were determined (Drozdz and Eberle, 1995). Radioiodination of the tyrosine at position thirteen resulted in a ligand with dramatically reduced biological activity (see Drozdz and Eberle, 1995). In contrast, the radioiodination of the MCH analogue [Phe$^{13}$, Tyr$^{19}$]-MCH was successful (Drozdz et al., 1995); the ligand retained biological activity and exhibited specific binding to a variety of cell lines including mouse melanoma (B16-F1, G4F, and G4F-7), PC12, and COS cells. In G4F-7 cells, the $K_D$=0.118 nM and the $B_{max}$~1100 sites/cell. Importantly, the binding was not inhibited by α-MSH but was weakly inhibited by rat ANF (Ki=116 nM vs. 12 nM for native MCH) (Drozdz et al., 1995). More recently specific MCH binding was reported in transformed keratinocytes (Burgaud et al., 1997) and melanoma cells (Drozdz et al., 1998), where photo-crosslinking studies suggest that the receptor is a membrane protein with an apparent molecular weight of 45–50 kDaltons, compatible with the molecular weight range of the GPCR superfamily of receptors. No radioautoradiographic studies of MCH receptor localization using this ligand have been reported as yet.

Signal transduction mechanisms for MCH receptors remain obscure. No direct evidence supporting G-protein coupling exists in mammals, but two lines of weak evidence exist in teleost fish for $G_{αq}$- and/or $G_{αi}$-type coupling: 1) indirect evidence exists for MCH acting via phospholipase C in teleost fish melanophores (phospholipase C inhibitors and protein kinase C inhibitors shift the MCH dose-response curve to the right, and TPA mimics MCH at low doses (Abrao et al., 1991)); and 2) MCH-elicited pigment aggregation in fish melanophores is associated with a reduction in basal cAMP levels, similar to that observed with norepinephrine (Svensson et al., 1991; Morishita et al., 1993). Arguing against G-protein coupling is the general structural homology of MCH with ANF, whose receptors are not in the GPCR superfamily. Recently the actions of MCH were reported to be mediated via activation of a phosphatidylinositol-3-kinase pathway which is typical of tyrosine kinase and cytokine receptors (Qu et al., 1998); however, since multiple signaling pathways (receptor cross talk) may produce this mediator no conclusions can be reached regarding MCH signal transduction pathways in mammalian systems.

The localization and biological activities of MCH peptide suggest that the modulation of MCH receptor activity may be useful in a number of therapeutic applications. The role of MCH in feeding is the best characterized of its potential clinical uses. MCH is expressed in the lateral hypothalamus, a brain area implicated in the regulation of thirst and hunger (Grillon et al., 1997); recently orexins A and B, which are potent orexigenic agents, have been shown to have very similar localization to MCH in the lateral hypothalamus (Sakurai et al., 1998). MCH mRNA levels in this brain region are increased in rats after 24 hours of food-deprivation (Hervé and Fellman, 1997); after insulin injection, a significant increase in the abundance and staining intensity of MCH immunoreactive perikarya and fibres was observed concurrent with a significant increase in the level of MCH mRNA (Bahjaoui-Bouhaddi et al., 1994). Consistent with the ability of MCH to stimulate feeding in rats (Rossi et al., 1997) is the observation that MCH mRNA levels are upregulated in the hypothalami of obese ob/ob mice (Qu et al., 1996), and decreased in the hypothalami of rats treated with leptin, whose food intake and body weight gains are also decreased (Sahu, 1998). MCH appears to act as a functional antagonist of the melanocortin system in its effects on food intake and on hormone secretion within the HPA (hypothalamopituitary/adrenal axis) (Ludwig et al., 1998). Together these data suggest a role for endogenous MCH in the regulation of energy balance and response to stress, and provide a rationale for the development of specific compounds acting at MCH receptors for use in the treatment of obesity and stress-related disorders.

In all species studied to date, a major portion of the neurons of the MCH cell group occupies a rather constant location in those areas of the lateral hypothalamus and subthalamus where they lie and may be a part of some of the so-called "extrapyramidal" motor circuits. These involve substantial striato- and pallidofugal pathways involving the thalamus and cerebral cortex, hypothalamic areas, and reciprocal connections to subthalamic nucleus, substantia nigra, and mid-brain centers (Bittencourt et al., 1992). In their location, the MCH cell group may offer a bridge or mechanism for expressing hypothalamic visceral activity with appropriate and coordinated motor activity. Clinically it may be of some value to consider the involvement of this MCH system in movement disorders, such as Parkinson's disease and Huntingdon's Chorea in which extrapyramidal circuits are known to be involved.

Human genetic linkage studies have located authentic hMCH loci on chromosome 12 (12q23–24) and the variant hMCH loci on chromosome 5 (5q12–13) (Pedeutour et al., 1994). Locus 12q23–24 coincides with a locus to which autosomal dominant cerebellar ataxia type II (SCA2) has been mapped (Auburger et al., 1992; Twells et al., 1992). This disease comprises neurodegenerative disorders, including an olivopontocerebellar atrophy. Furthermore, the gene for Darier's disease, has been mapped to locus 12q23–24 (Craddock et al., 1993). Dariers' disease is characterized by abnormalities I keratinocyte adhesion and mental illnesses in some families. In view of the functional and neuroanatomical patterns of the MCH neural system in the rat and human brains, the MCH gene may represent a good candidate for SCA2 or Darier's disease. Interestingly, diseases with high social impact have been mapped to this locus. Indeed, the gene responsible for chronic or acute forms of spinal muscular atrophies has been assigned to chromosome 5q12–13 using genetic linkage analysis (Melki et al., 1990; Westbrook et al., 1992). Furthermore, independent lines of evidence support the assignment of a major schizophrenia locus to chromosome 5q11.2–13.3 (Sherrington et al., 1988; Bassett et al., 1988; Gilliam et al., 1989). The above studies suggest that MCH may play a role in neurodegenerative diseases and disorders of emotion.

Additional therapeutic applications for MCH-related compounds are suggested by the observed effects of MCH in other biological systems. For example, MCH may regulate reproductive functions in male and female rats. MCH transcripts and MCH peptide were found within germ cells in testes of adult rats, suggesting that MCH may participate in stem cell renewal and/or differentiation of early spermatocytes (Hervieu et al., 1996). MCH injected directly into the medial preoptic area (MPOA) or ventromedial nucleus (VMN) stimulated sexual activity in female rats (Gonzalez et al., 1996). In ovariectomized rats primed with estradiol, MCH stimulated luteinizing hormone (LH) release while anti-MCH antiserum inhibited LH release (Gonzalez et al., 1997). The zona incerta, which contains a large population of MCH cell bodies, has previously been identified as a regulatory site for the pre-ovulatory LH surge (MacKenzie et al., 1984). MCH has been reported to influence release of pituitary hormones including ACTH and oxytocin. MCH analogues may also be useful in treating epilepsy. In the PTZ seizure model, injection of MCH prior to seizure induction prevented seizure activity in both rats and guinea pigs, suggesting that MCH-containing neurons may participate in the neural circuitry underlying PTZ-induced seizure (Knigge and Wagner, 1997). MCH has also been observed to affect behavioral correlates of cognitive functions. MCH treatment hastened extinction of the passive avoidance response in rats (McBride et al., 1994), raising the possibility that MCH receptor antagonists may be beneficial for memory storage and/or retention. A possible role for MCH in the modulation or perception of pain is supported by the dense innervation of the periaqueductal grey (PAG) by MCH-positive fibers. Finally, MCH may participate in the regulation of fluid intake. ICV infusion of MCH in conscious sheep produced diuretic, natriuretic, and kaliuretic changes in response to increased plasma volume (Parkes, 1996). Together with anatomical data reporting the presence of MCH in fluid regulatory areas of the brain, the results indicate that MCH may be an important peptide involved in the central control of fluid homeostasis in mammals.

SUMMARY OF THE INVENTION

This invention provides an isolated nucleic acid encoding a human MCH1 receptor.

This invention provides a nucleic acid encoding a human MCH1 receptor, wherein the nucleic acid (a) hybridizes to a nucleic acid having the defined sequence shown in FIG. 1 (Seq. ID No. 1) under low stringency conditions or a sequence complementary thereto and (b) is further characterized by its ability to cause a change in the pH of a culture of CHO cells when an MCH1 ligand is added to the culture and the CHO cells contain the nucleic acid which hybridized to the nucleic acid having the defined sequence or its complement.

This invention provides a purified human MCH1 receptor protein.

This invention provides a vector comprising a nucleic acid encoding a human MCH1 receptor, particularly a vector adapted for expression of the human MCH1 receptor in mammalian or non-mammalian cells. One such vector is a plasmid designated pEXJ.HR-TL231 (ATCC Accession No. 203197) which comprises a nucleotide sequence encoding a human MCH1 receptor.

This invention also provides a cell comprising a vector which comprises a nucleic acid encoding a human MCH1 receptor as well as a membrane preparation isolated from such cells.

This invention further provides a nucleic acid probe comprising at least 15 nucleotides which specifically hybridizes with a nucleic acid encoding a mammalian MCH1 receptor, wherein the probe has a unique sequence corresponding to a sequence present within the nucleic acid which encodes the human MCH1 receptor or its complement, both of which are present in plasmid pEXJ.HR-TL231 (ATCC Accession No. 203197).

This invention further provides a nucleic acid probe comprising at least 15 nucleotides which specifically hybridizes with a nucleic acid encoding a mammalian MCH1 receptor, wherein the probe has a unique sequence corresponding to a sequence present within (a) the nucleic acid sequence shown in FIG. 1 (Seq. I.D. No. 1) or (b) the reverse complement thereof.

This invention also provides an antisense oligonucleotide having a sequence capable of specifically hybridizing an RNA encoding a human MCH1 receptor, so as to prevent translation of the RNA and an antisense oligonucleotide having a sequence capable of specifically hybridizing to the genomic DNA encoding a human MCH1 receptor.

This invention further provides an antibody capable of binding to a human MCH1 receptor as well as an agent capable of competitively inhibiting the binding of the antibody to a human MCH1 receptor.

This invention provides a pharmaceutical composition comprising (a) an amount of the oligonucleotide described above capable of passing through a cell membrane and effective to reduce expression of a human MCH1 receptor and (b) a pharmaceutically acceptable carrier capable of passing through the cell membrane.

Moreover, this invention provides a transgenic, nonhuman mammal expressing DNA encoding a human MCH1 receptor. This invention also provides a transgenic, nonhuman mammal comprising a homologous recombination knockout of the native human MCH1 receptor. This invention further provides a transgenic, nonhuman mammal whose genome comprises antisense DNA complementary to the DNA encoding a human MCH1 receptor so placed within the genome as to be transcribed into antisense mRNA which is complementary to mRNA encoding the human MCH1 receptor and which hybridizes to mRNA encoding the human MCH1 receptor, thereby reducing its translation.

In one embodiment this invention provides a process for identifying a chemical compound which specifically binds to a mammalian MCH1 receptor which comprises contacting cells containing DNA encoding and expressing on their cell surface a mammalian MCH1 receptor, wherein such cells do not normally express the mammalian MCH1 receptor, with the compound under conditions suitable for binding, and detecting specific binding of the chemical compound to the mammalian MCH1 receptor.

This invention provides a process for identifying a chemical compound which specifically binds to a mammalian MCH1 receptor which comprises contacting a membrane preparation from cells transfected with DNA encoding and expressing on their cell surface the mammalian MCH1 receptor, wherein such cells do not normally express the mammalian MCH1 receptor, with the compound under conditions suitable for binding, and detecting specific binding of the chemical compound to the mammalian MCH1 receptor.

This invention provides a process involving competitive binding for identifying a chemical compound which specifically binds to a mammalian MCH1 receptor which comprises separately contacting cells expressing on their cell surface the mammalian MCH1 receptor, wherein such cells do not normally express the mammalian MCH1 receptor, with both the chemical compound and a second chemical compound known to bind to the receptor, and with only the second chemical compound, under conditions suitable for binding of both compounds, and detecting specific binding of the chemical compound to the mammalian MCH1 receptor, a decrease in the binding of the second chemical compound to the mammalian MCH1 receptor in the presence of the chemical compound indicating that the chemical compound binds to the mammalian MCH1 receptor.

This invention provides a process involving competitive binding for identifying a chemical compound which specifically binds to a mammalian MCH1 receptor which comprises separately contacting a membrane fraction from a cell extract of cells expressing on their cell surface the mammalian MCH1 receptor, wherein such cells do not normally express the mammalian MCH1 receptor, with both the chemical compound and a second chemical compound known to bind to the receptor, and with only the second chemical compound, under conditions suitable for binding of both compounds, and detecting specific binding of the chemical compound to the mammalian MCH1 receptor, a decrease in the binding of the second chemical compound to the mammalian MCH1 receptor in the presence of the chemical compound indicating that the chemical compound binds to the mammalian MCH1 receptor.

This invention provides a method of screening a plurality of chemical compounds not known to bind to a mammalian MCH1 receptor to identify a compound which specifically binds to the mammalian MCH1 receptor, which comprises (a) contacting cells transfected with and expressing DNA encoding the mammalian MCH1 receptor with a compound known to bind specifically to the mammalian MCH1 receptor; (b) contacting the preparation of step (a) with the plurality of compounds not known to bind specifically to the mammalian MCH1 receptor, under conditions permitting binding of compounds known to bind the mammalian MCH1 receptor; (c) determining whether the binding of the compound known to bind to the mammalian MCH1 receptor is reduced in the presence of the compounds within the plurality of compounds, relative to the binding of the compound in the absence of the plurality of compounds; and if so (d) separately determining the binding to the mammalian MCH1 receptor of compounds included in the plurality of compounds, so as to thereby identify the compound which specifically binds to the mammalian MCH1 receptor.

This invention provides a method of screening a plurality of chemical compounds not known to bind to a mammalian MCH1 receptor to identify a compound which specifically binds to the mammalian MCH1 receptor, which comprises (a) contacting a membrane preparation from cells transfected with and expressing DNA encoding a mammalian MCH1 receptor with a compound known to bind specifically to the mammalian MCH1 receptor; (b) contacting the preparation of step (a) with the plurality of compounds not known to bind specifically to the mammalian MCH1 receptor, under conditions permitting binding of compounds known to bind the mammalian MCH1 receptor; (c) determining whether the binding of the compound known to bind to the mammalian MCH1 receptor is reduced in the presence of the compounds within the plurality of compounds, relative to the binding of the compound in the absence of the plurality of compounds; and if so (d) separately determining the binding to the mammalian MCH1 receptor of compounds included in the plurality of compounds, so as to thereby identify the compound which specifically binds to the mammalian MCH1 receptor.

This invention provides a method of detecting expression of a mammalian MCH1 receptor by detecting the presence of mRNA coding for the mammalian MCH1 receptor which comprises obtaining total mRNA from the cell and contacting the mRNA so obtained with a nucleic acid probe under hybridizing conditions, detecting the presence of mRNA hybridizing to the probe, and thereby detecting the expression of the mammalian MCH1 receptor by the cell.

This invention provides a method of detecting the presence of a mammalian MCH1 receptor on the surface of a cell which comprises contacting the cell with an antibody under conditions permitting binding of the antibody to the receptor, detecting the presence of the antibody bound to the cell, and thereby detecting the presence of the mammalian MCH1 receptor on the surface of the cell.

This invention provides a method of determining the physiological effects of varying levels of activity of human MCH1 receptors which comprises producing a transgenic, nonhuman mammal whose levels of human MCH1 receptor activity are varied by use of an inducible promoter which regulates human MCH1 receptor expression.

This invention provides a method of determining the physiological effects of varying levels of activity of human MCH1 receptors which comprises producing a panel of transgenic, nonhuman mammals each expressing a different amount of human MCH1 receptor.

This invention provides a method for identifying an antagonist capable of alleviating an abnormality wherein the abnormality is alleviated by decreasing the activity of a human MCH1 receptor comprising administering a compound to the transgenic, nonhuman mammal and determining whether the compound alleviates the physical and behavioral abnormalities displayed by the transgenic, nonhuman mammal as a result of overactivity of a human MCH1 receptor, the alleviation of the abnormality identifying the compound as an antagonist. This invention also provides an antagonist identified by this method. This invention further provides a pharmaceutical composition comprising an antagonist identified by this method and a pharmaceutically acceptable carrier.

This invention provides a method of treating an abnormality in a subject wherein the abnormality is alleviated by decreasing the activity of a human MCH1 receptor which comprises administering to the subject an effective amount of this pharmaceutical composition, thereby treating the abnormality.

This invention provides a method for identifying an agonist capable of alleviating an abnormality in a subject wherein the abnormality is alleviated by increasing the activity of a human MCH1 receptor comprising administering a compound to a transgenic, nonhuman mammal, and determining whether the compound alleviates the physical and behavioral abnormalities displayed by the transgenic, nonhuman mammal, the alleviation of the abnormality identifying the compound as an agonist. This invention also provides an agonist identified by this method. This invention further provides a pharmaceutical composition comprising an agonist identified by this method and a pharmaceutically acceptable carrier. This invention provides a method of treating an abnormality in a subject wherein the abnormality is alleviated by increasing the activity of a human MCH1 receptor which comprises administering to the subject an effective amount of this pharmaceutical composition, thereby treating the abnormality.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a human MCH1 receptor and labeled with a detectable marker; (e) detecting labeled bands which have hybridized to the DNA encoding a human MCH1 receptor labeled with a detectable marker to create a unique band pattern specific to the DNA of subjects suffering from the disorder; (f) preparing DNA obtained for diagnosis by steps (a)–(e); and (g) comparing the unique band pattern specific to the DNA of subjects suffering from the disorder from step (e) and the DNA obtained for diagnosis from step (f) to determine whether the patterns are the same or different and to diagnose thereby predisposition to the disorder if the patterns are the same.

This invention provides a method of preparing a purified human MCH1 receptor which comprises: (a) inducing cells to express the human MCH1 receptor; (b) recovering the human MCH1 receptor from the induced cells; and (c) purifying the human MCH1 receptor so recovered.

This invention provides a method of preparing a purified human MCH1 receptor which comprises: (a)inserting nucleic acid encoding the human MCH1 receptor in a suitable vector; (b) introducing the resulting vector in a suitable host cell; (c) placing the resulting cell in suitable condition permitting the production of the isolated human MCH1 receptor; (d) recovering the human MCH1 receptor produced by the resulting cell; and (e) purifying the human MCH1 receptor so recovered.

This invention provides a process for determining whether a chemical compound is a mammalian MCH1 receptor agonist which comprises contacting cells transfected with and expressing DNA encoding the mammalian MCH1 receptor with the compound under conditions permitting the activation of the mammalian MCH1 receptor, and detecting an increase in mammalian MCH1 receptor activity, so as to thereby determine whether the compound is a mammalian MCH1 receptor agonist. This invention also provides a pharmaceutical composition which comprises an amount of a mammalian MCH1 receptor agonist determined by this process effective to increase activity of a mammalian MCH1 receptor and a pharmaceutically acceptable carrier.

This invention provides a process for determining whether a chemical compound is a mammalian MCH1 receptor antagonist which comprises contacting cells transfected with and expressing DNA encoding the mammalian MCH1 receptor with the compound in the presence of a known mammalian MCH1 receptor agonist, under conditions permitting the activation of the mammalian MCH1 receptor, and detecting a decrease in mammalian MCH1 receptor activity, so as to thereby determine whether the compound is a mammalian MCH1 receptor antagonist. This invention also provides a pharmaceutical composition which comprises an amount of a mammalian MCH1 receptor antagonist determined by this process effective to reduce activity of a mammalian MCH1 receptor and a pharmaceutically acceptable carrier.

This invention provides a process for determining whether a chemical compound specifically binds to and activates a mammalian MCH1 receptor, which comprises contacting cells producing a second messenger response and expressing on their cell surface the mammalian MCH1 receptor, wherein such cells do not normally express the mammalian MCH1 receptor, with the chemical compound under conditions suitable for activation of the mammalian MCH1 receptor, and measuring the second messenger response in the presence and in the absence of the chemical compound, a change in the second messenger response in the presence of the chemical compound indicating that the compound activates the mammalian MCH1 receptor. This invention also provides a compound determined by this process. This invention further provides a pharmaceutical composition which comprises an amount of the compound (a MCH1 receptor agonist) determined by this process effective to increase activity of a mammalian MCH1 receptor and a pharmaceutically acceptable carrier.

This invention provides a process for determining whether a chemical compound specifically binds to and inhibits activation of a mammalian MCH1 receptor, which comprises separately contacting cells producing a second messenger response and expressing on their cell surface the mammalian MCH1 receptor, wherein such cells do not normally express the mammalian MCH1 receptor, with both the chemical compound and a second chemical compound known to activate the mammalian MCH1 receptor, and with only the second chemical compound, under conditions suitable for activation of the mammalian MCH1 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian MCH1 receptor. This invention also provides a compound determined by this process. This invention further provides a pharmaceutical composition which comprises an amount of the compound (a mammalian MCH1 receptor antagonist) determined by this effective to reduce activity of a mammalian MCH1 receptor and a pharmaceutically acceptable carrier.

This invention provides a method of screening a plurality of chemical compounds not known to activate a mammalian MCH1 receptor to identify a compound which activates the mammalian MCH1 receptor which comprises: (a) contacting cells transfected with and expressing the mammalian MCH1 receptor with the plurality of compounds not known to activate the mammalian MCH1 receptor, under conditions permitting activation of the mammalian MCH1 receptor; (b) determining whether the activity of the mammalian MCH1 receptor is increased in the presence of the compounds; and if so (c) separately determining whether the activation of the mammalian MCH1 receptor is increased by each compound included in the plurality of compounds, so as to thereby identify the compound which activates the mammalian MCH1 receptor. This invention also provides a compound identified by this method. This invention further provides a pharmaceutical composition which comprises an amount of the compound (a mammalian MCH1 receptor agonist) identified by this method effective to increase activity of a mammalian MCH1 receptor and a pharmaceutically acceptable carrier.

This invention provides a method of screening a plurality of chemical compounds not known to inhibit the activation of a mammalian MCH1 receptor to identify a compound which inhibits the activation of the mammalian MCH1 receptor, which comprises: (a) contacting cells transfected with and expressing the mammalian MCH1 receptor with the plurality of compounds in the presence of a known mammalian MCH1 receptor agonist, under conditions permitting activation of the mammalian MCH1 receptor; (b) determining whether the activation of the mammalian MCH1 receptor is reduced in the presence of the plurality of compounds, relative to the activation of the mammalian MCH1 receptor in the absence of the plurality of compounds; and if so (c) separately determining the inhibition of activation of the mammalian MCH1 receptor for each compound included in the plurality of compounds, so as to thereby identify the compound which inhibits the activation of the mammalian MCH1 receptor. This invention also provides a compound identified by this method. This invention further provides a pharmaceutical composition which comprises an amount of the compound (a mammalian MCH1 receptor antagonist) identified by this process effective to decrease activity of a mammalian MCH1 receptor and a pharmaceutically acceptable carrier.

This invention provides a method of treating an abnormality in a subject wherein the abnormality is alleviated by increasing the activity of a mammalian MCH1 receptor which comprises administering to the subject an amount of a compound which is a mammalian MCH1 receptor agonist effective to treat the abnormality.

This invention provides a method of treating an abnormality in a subject wherein the abnormality is alleviated by decreasing the activity of a mammalian MCH1 receptor which comprises administering to the subject an amount of a compound which is a mammalian MCH1 receptor antagonist effective to treat the abnormality.

This invention provides a process for making a composition of matter which specifically binds to a mammalian MCH1 receptor which comprises identifying a chemical compound using any of the processes described herein for identifying a compound which binds to and/or activates or inhibits activation of a mammalian MCH1 receptor and then synthesizing the chemical compound or a novel structural and functional analog or homolog thereof. This invention further provides a process for preparing a pharmaceutical composition which comprises administering a pharmaceutically acceptable carrier and a pharmaceutically acceptable amount of a chemical compound identified by any of the processes described herein for identifying a compound which binds to and/or activates or inhibits activation of a mammalian MCH1 receptor or a novel structural and functional analog or homolog thereof.

BRIEF DESCRIPTION OF THE FIGURES

FIG. 1 Nucleotide sequence encoding a human MCH1 receptor (MCH1) (Seq. I.D. No. 1). Three potential start (ATG) codons and the stop (TGA) codon are underlined.

FIG. 2 Deduced amino acid sequence (Seq. I.D. No. 2) of the human MCH1 receptor (MCH1) encoded by the nucleotide sequence shown FIG. 1 (Seq. I.D. No. 1).

FIG. 3 Deduced amino acid sequence for human MCH1 (SEQ. ID No. 2). The seven putative transmembrane (TM) regions are underlined.

FIG. 4 Nucleotide sequence of rat MCH1 (SEQ. ID No. 3). One start (ATG) codon and the stop codon (TGA) are underlined.

FIG. 5 Deduced amino acid sequence for rat MCH1 (SEQ. ID No. 4).

FIG. 10 Binding of [$^{125}$I]Phe$^{13}$,Tyr$^{19}$-MCH on MCH1-transfected Cos-7 cell membranes. Results are means±S.E.M. (vertical lines) of triplicate determinations.

DETAILED DESCRIPTION OF THE INVENTION

Figure 6:
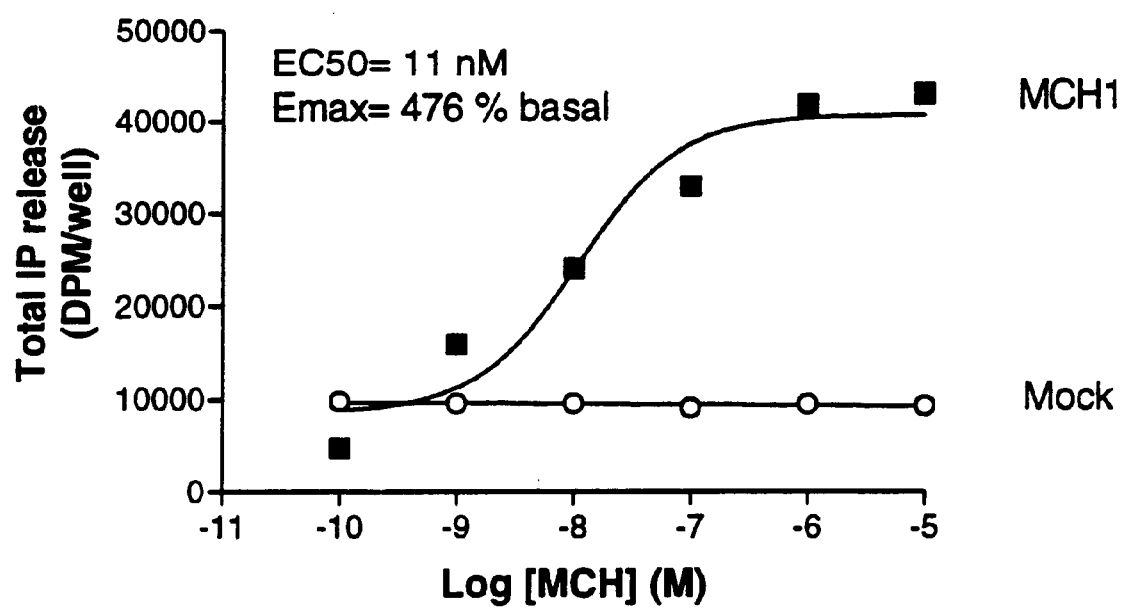
FIG. 6 MCH1-mediated ID dose response to MCH.

Throughout this application, the following standard abbreviations are used to indicate specific nucleotide bases:

A=adenine
G=guanine
C=cytosine
T=thymine
U=uracil
M=adenine or cytosine
R=adenine or guanine
W=adenine, thymine, or uracil
S=cytosine or guanine
Y=cytosine, thymine, or uracil
K=guanine, thymine, or uracil
V=adenine, cytosine, or guanine (not thymine or uracil)
H=adenine, cytosine, thymine, or uracil (not guanine)
D=adenine, guanine, thymine, or uracil (not cytosine)
B=cytosine, guanine, thymine, or uracil (not adenine)
N=adenine, cytosine, guanine, thymine, or uracil (or other modified base such as inosine)
I=inosine Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

The activity of a G-protein coupled receptor such as the polypeptides disclosed herein may be measured using any of a variety of functional assays in which activation of the receptor in question results in an observable change in the level of some second messenger system, including, but not limited to, adenylate cyclase, calcium mobilization, arachidonic acid release, ion channel activity, inositol phospholipid hydrolysis or guanylyl cyclase. Heterologous expression systems utilizing appropriate host cells to express the nucleic acid of the subject invention are used to obtain the desired second messenger coupling. Receptor activity may also be assayed in an oocyte expression system.

It is possible that the human MCH1 receptor gene contains introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene. (Burns et al., 1996; Chu et al., 1996). Such variants may exhibit pharmacologic properties differing from the polypeptide encoded by the original gene.

This invention provides splice variants of the human MCH1 receptor disclosed herein. This invention further provides for alternate translation initiation sites and alternately spliced or edited variants of nucleic acids encoding the human MCH1 receptor of this invention.

The nucleic acid of the subject invention also includes nucleic acid analogs of the human MCH1 receptor gene, wherein the human MCH1 receptor gene comprises the nucleic acid sequence shown in FIG. 1 or contained in plasmid pEXJ.HR-TL231 (ATCC Accession No. 203197). Nucleic acid analogs of the human MCH1 receptor genes differ from the human MCH1 receptor gene described herein in terms of the identity or location of one or more nucleic acid bases (deletion analogs containing less than all of the nucleic acid bases shown in FIG. 1 or contained in plasmid pEXJ.HR-TL231, substitution analogs wherein one or more nucleic acid bases shown in FIG. 1 or contained in plasmids pEXJ.HR-TL231 are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIG. 1 or contained in plasmid pEXJ.HR-TL231. In one embodiment of the present invention, the nucleic acid analog encodes a protein which comprises an amino acid sequence as shown in FIG. 2 or encoded by the nucleic acid sequence contained in plasmid pEXJ.HR-TL231. In another embodiment, the nucleic acid analog encodes a protein comprising an amino acid sequence which differs from the amino acid sequences shown in FIG. 2 or encoded by the nucleic acid contained in plasmids pEXJ.HR-TL231. In a further embodiment, the protein encoded by the nucleic acid analog has a function which is the same as the function of the receptor protein comprising the amino acid sequence shown in FIG. 2. In another embodiment, the function of the protein encoded by the nucleic acid analog differs from the function of the receptor protein comprising the amino acid sequence shown in FIG. 2. In another embodiment, the variation in the nucleic acid sequence occurs within the transmembrane (TM) region of the protein. In a further embodiment, the variation in the nucleic acid sequence occurs outside of the TM region.

This invention provides the above-described isolated nucleic acid, wherein the nucleic acid is DNA. In an embodiment, the DNA is cDNA. In another embodiment, the DNA is genomic DNA. In still another embodiment, the nucleic acid is RNA. Methods for production and manipulation of nucleic acid molecules are well known in the art.

This invention further provides nucleic acid which is degenerate with respect to the DNA encoding the polypeptides described herein. In an embodiment, the nucleic acid comprises a nucleotide sequence which is degenerate with respect to the nucleotides sequence shown in FIG. 1 (SEQ ID NO. 2) or the nucleotide sequence contained in the plasmid pEXJ.HR-TL231, that is, a nucleotide sequence which is translated into the same amino acid sequence.

This invention also encompasses DNAs and cDNAs which encode amino acid sequences which differ from those of the polypeptides of this invention, but which should not produce phenotypic changes. Alternately, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. The creation of polypeptide analogs is well known to those of skill in the art (R. F. Spurney et al. (1997); Fong, T. M. et al. (1995); Underwood, D. J. et al. (1994); Graziano, M. P. et al. (1996); Guan X. M. et al. (1995)).

The modified polypeptides of this invention may be transfected into cells either transiently or stably using methods well-known in the art, examples of which are disclosed herein. This invention also provides for binding assays using the modified polypeptides, in which the polypeptide is expressed either transiently or in stable cell lines. This invention further provides a compound identified using a modified polypeptide in a binding assay such as the binding assays described herein.

The nucleic acids described and claimed herein are useful for the information which they provide concerning the amino acid sequence of the polypeptide and as products for the large scale synthesis of the polypeptides by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention provides an isolated nucleic acid encoding a human MCH1 receptor. In one embodiment, the nucleic acid is DNA. In another embodiment, the DNA is cDNA. In another embodiment, the DNA is genomic DNA. In another embodiment, the nucleic acid is RNA.

This invention also provides methods of using an isolated nucleic acid encoding species homologs of the MCH1 receptor encoded by the nucleic acid sequence shown in FIG. 1 (Seq. ID No. 1) or encoded by the plasmid pEXJ.HR-TL231. In one embodiment, the nucleic acid encodes a mammalian MCH1 receptor homolog which has substantially the same amino acid sequence as does the MCH1 receptor encoded by the plasmid pEXJ.HR-TL231. In another embodiment, the nucleic acid encodes a mammalian MCH1 receptor homolog which has above 65% amino acid identity to the MCH1 receptor encoded by the plasmid pEXJ.HR-TL231; preferably above 75% amino acid identity to the MCH1 receptor encoded by the plasmid pEXJ.HR-TL231; more preferably above 85% amino acid identity to the MCH1 receptor encoded by the plasmid pEXJ.HR-TL231; most preferably above 95% amino acid identity to the MCH1 receptor encoded by the plasmid pEXJ.HR-TL231. In another embodiment, the mammalian MCH1 receptor homolog has above 70% nucleic acid identity to the MCH1 receptor gene contained in plasmid pEXJ.HR-TL231; preferably above 80% nucleic acid identity to the MCH1 receptor gene contained in the plasmid pEXJ.HR-TL231; more preferably above 90% nucleic acid identity to the MCH1 receptor gene contained in the plasmid pEXJ.HR-TL231. Examples of methods for isolating and purifying species homologs are described elsewhere (e.g., U.S. Pat. No. 5,602,024, WO94/14957, WO97/26853, WO98/15570).

In a separate embodiment of the present invention, the nucleic acid encodes a MCH1 receptor which has an amino acid sequence identical to that encoded by the plasmid pEXJ.HR-TL231. In a further embodiment, the MCH1 receptor comprises a sequence substantially the same as the amino acid sequence shown in FIG. 2 (Seq. I.D. No. 2). In another embodiment, the MCH1 receptor comprises an amino acid sequence as shown in FIG. 2 (Seq. I.D. No. 2).

In separate embodiments, the human MCH1 receptor is encoded by the nucleic acid sequence shown in FIG. 1 beginning with any of the three indicated start (ATG) codons.

This invention provides an isolated nucleic acid encoding a modified human MCH1 receptor, which differs from a human MCH1 receptor by having an amino acid(s) deletion, replacement, or addition in the third intracellular domain.

This invention provides a nucleic acid encoding a human MCH1 receptor, wherein the nucleic acid (a) hybridizes to a nucleic acid having the defined sequence shown in FIG. 1 (Seq. ID No. 1) under low stringency conditions or a sequence complementary thereto and (b) is further characterized by its ability to cause a change in the pH of a culture of CHO cells when a MCH1 ligand is added to the culture and the CHO cells contain the nucleic acid which hybridized to the nucleic acid having the defined sequence or its complement. Hybridization at low stringency is performed at 40° C. in a hybridization buffer containing 25% formamide, 5×SCC, 7 mM Tris, 1×Denhardt's, 25 $\mu$l/ml salmon sperm DNA. Wash at 40° C. in 0.1×SCC, 0.1% SDS. Changes in pH are measured through microphysiometric measurement of receptor mediated extracellular acidification rates. Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway. General guidelines for transient receptor expression, cell preparation and microphysiometric recording are described elsewhere (Salon, J. A. and Owicki, J. A., 1996). Receptors and/or control vectors are transiently expressed in CHO-K1 cells, by liposome mediated transfection according to the manufacturers recommendations (LipofectAMINE, GibcoBRL, Gaithersburg, Md.), and maintained in Ham's F-12 complete (10% serum). A total of 10 $\mu$g of DNA is used to transfect each 75 cm flask which had been split 24 hours prior to the transfection and judged to be 70–80% confluent at the time of transfection. 24 hours post transfection, the cells are harvested and $3\times10^5$ cells seeded into microphysiometer capsules. Cells are allowed to attach to the capsule membrane for an additional 24 hours; during the last 16 hours, the cells are switched to serum-free F-12 complete to minimize ill-defined metabolic stimulation caused by assorted serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established. A standard recording protocol specifies a 100 µl/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 µM final concentration. Ligand samples are then washed out and the acidification rates reported are expressed as a percentage increase of the peak response over the baseline rate observed just prior to challenge. An examples of a MCH ligand includes, but is not limited to, the endogenous MCH peptide.

This invention provides a purified human MCH1 receptor protein.

This invention provides a vector comprising nucleic acid encoding a human MCH1 receptor. In an embodiment, the vector is adapted for expression in a cell which comprises the regulatory elements necessary for expression of the nucleic acid in the cell operatively linked to the nucleic acid encoding the human MCH1 receptor as to permit expression thereof. In separate embodiments, the cell is a bacterial cell, an amphibian cell, a yeast cell, an insect cell or a mammalian cell. In another embodiment, the vector is a baculovirus. In one embodiment, the vector is a plasmid.

This invention provides a plasmid designated pEXJ.HR-TL231 (ATCC Accession No. 203197). This plasmid comprises the regulatory elements necessary for expression of DNA in a mammalian cell operatively linked to DNA encoding the human MCH1 receptor so as to permit expression thereof.

This plasmid (pEXJ.HR-TL231) was deposited on Sep. 17, 1998, with the American Type Culture Collection (ATCC), 10801 University Boulevard, Manassas, Va. 20110-2209, U.S.A. under the provisions of the Budapest Treaty for the International Recognition of the Deposit of Microorganisms for the Purposes of Patent Procedure and was accorded ATCC Accession No. 203197.

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides a cell comprising a vector comprising a nucleic acid encoding the human MCH1 receptor. In an embodiment, the cell is a non-mammalian cell. In a further embodiment, the non-mammalian cell is a Xenopus oocyte cell or a Xenopus melanophore cell. In another embodiment, the cell is a mammalian cell. In a further embodiment, the mammalian cell is a COS-7 cell, a 293 human embryonic kidney cell, a NIH-3T3 cell, a LM(tk-) cell, a mouse Y1 cell, or a CHO cell.

This invention provides an insect cell comprising a vector adapted for expression in an insect cell which comprises a nucleic acid encoding a human MCH1 receptor. In another embodiment, the insect cell is an Sf9 cell, an Sf21 cell or a Trichoplusia ni 5Bl-4 (HighFive) cell.

This invention provides a membrane preparation isolated from any one of the cells described above.

This invention provides a nucleic acid probe comprising at least 15 nucleotides, which probe specifically hybridizes with a nucleic acid encoding a human MCH1 receptor, wherein the probe has a unique sequence corresponding to a sequence present within one of the two strands of the nucleic acid encoding a human MCH1 receptor present in plasmid pEXJ.HR-TL231. This invention also provides a nucleic acid probe comprising at least 15 nucleotides, which probe specifically hybridizes with a nucleic acid encoding a human MCH1 receptor, wherein the probe has a unique sequence corresponding to a sequence present within (a) the nucleic acid sequence shown in FIG. 1 (Seq. I.D. No. 1) or (b) the reverse complement thereto. In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

Nucleic acid probe technology is well known to those skilled in the art who will readily appreciate that such probes may vary greatly in length and may be labeled with a detectable label, such as a radioisotope or flourescent dye, to facilitate, detection of the probe. DNA probe molecules may be produced by insertion of a DNA molecule which encodes the polypeptides of this invention into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the polypeptides of this invention downstream of a bacteriophage promoter such as T3, T7, or SP6. Large amounts of RNA probe may be produced by incubating the labeled nucleotides with the linearized fragment where it contains an upstream promoter in the presence of the appropriate RNA polymerase.

This invention provides an antisense oligonucleotide having a sequence capable of specifically hybridizing to RNA encoding a human MCH1 receptor, so as to prevent translation of the RNA. This invention also provides an antisense oligonucleotide having a sequence capable of specifically hybridizing to genomic DNA encoding a human MCH1 receptor. In one embodiment, the oligonucleotide comprises chemically modified nucleotides or nucleotide analogues.

This invention provides an antibody capable of binding to a human MCH1 receptor encoded by a nucleic acid encoding a human MCH1 receptor. This invention also provides an agent capable of competitively inhibiting the binding of the antibody to a human MCH1 receptor. In one embodiment, the antibody is a monoclonal antibody or antisera.

This invention provides a pharmaceutical composition comprising (a) an amount of the oligonucleotide capable of passing through a cell membrane and effective to reduce expression of a human MCH1 receptor and (b) a pharmaceutically acceptable carrier capable of passing through the cell membrane. In an embodiment, the oligonucleotide is coupled to a substance which inactivates mRNA. In a further embodiment, the substance which inactivates mRNA is a ribozyme. In another embodiment, the pharmaceutically acceptable carrier comprises a structure which binds to a human MCH1 receptor on a cell capable of being taken up by the cells after binding to the structure. In a further embodiment, the pharmaceutically acceptable carrier is capable of binding to a human MCH1 receptor which is specific for a selected cell type.

This invention provides a pharmaceutical composition which comprises an amount of an antibody effective to block binding of a ligand to a human MCH1 receptor and a pharmaceutically acceptable carrier.

As used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

This invention provides a transgenic, nonhuman mammal expressing DNA encoding a human MCH1 receptor. This invention also provides a transgenic, nonhuman mammal comprising a homologous recombination knockout of the native human MCH1 receptor. This invention further provides a transgenic, nonhuman mammal whose genome comprises antisense DNA complementary to the DNA encoding a human MCH1 receptor so placed within the genome as to be transcribed into antisense mRNA which is complementary to mRNA encoding the human MCH1 receptor and which hybridizes to mRNA encoding the human MCH1 receptor, thereby reducing its translation. In an embodiment, the DNA encoding the human MCH1 receptor additionally comprises an inducible promoter. In another embodiment, the DNA encoding the human MCH1 receptor additionally comprises tissue specific regulatory elements. In a further embodiment, the transgenic, nonhuman mammal is a mouse.

Animal model systems which elucidate the physiological and behavioral roles of the polypeptides of this invention are produced by creating transgenic animals in which the activity of the polypeptide is either increased or decreased, or the amino acid sequence of the expressed polypeptide is altered, by a variety of techniques. Examples of these techniques include, but are not limited to: 1) Insertion of normal or mutant versions of DNA encoding the polypeptide, by microinjection, electroporation, retroviral transfection or other means well known to those in the art, into appropriate fertilized embryos in order to produce a transgenic animal or 2) Homologous recombination of mutant or normal, human or animal versions of these genes with the native gene locus in transgenic animals to alter the regulation of expression or the structure of these polypeptide sequences. The technique of homologous recombination is well known in the art. It replaces the native gene with the inserted gene and so is useful for producing an animal that cannot express native polypeptides but does express, for example, an inserted mutant polypeptide, which has replaced the native polypeptide in the animal's genome by recombination, resulting in underexpression of the transporter. Microinjection adds genes to the genome, but does not remove them, and so is useful for producing an animal which expresses its own and added polypeptides, resulting in overexpression of the polypeptides.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a polypeptide of this invention is purified from a vector by methods well known in the art. Inducible promoters may be fused with the coding region of the DNA to provide an experimental means to regulate expression of the trans-gene. Alternatively, or in addition, tissue specific regulatory elements may be fused with the coding region to permit tissue-specific expression of the trans-gene. The DNA, in an appropriately buffered solution, is put into a microinjection needle (which may be made from capillary tubing using a pipette puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides a process for identifying a chemical compound which specifically binds to a mammalian MCH1 receptor which comprises contacting cells comprising DNA encoding, and expressing on their cell surface, the mammalian MCH1 receptor, with the compound under conditions suitable for binding, and detecting specific binding of the chemical compound to the mammalian MCH1 receptor, wherein the cells do not normally express the mammalian MCH1 receptor and the DNA encoding the mammalian MCH1 receptor (a) hybridizes to a nucleic acid having the defined sequence shown in FIG. 1 (Seq. ID No. 1) under low stringency conditions or a sequence complementary thereto and (b) is further characterized by its ability to cause a change in the pH of a culture of CHO cells when a MCH1 ligand is added to the culture and the CHO cells contain the nucleic acid which hybridized to the nucleic acid having the defined sequence or its complement. This invention also provides a process for identifying a chemical compound which specifically binds to a mammalian MCH1 receptor which comprises contacting a membrane preparation from cells comprising DNA encoding, and expressing on their cell surface, the mammalian MCH1 receptor, with the compound under conditions suitable for binding, and detecting specific binding of the chemical compound to the mammalian MCH1 receptor, wherein the cells do not normally express the mammalian MCH1 receptor and the DNA encoding the mammalian MCH1 receptor (a) hybridizes to a nucleic acid having the defined sequence shown in FIG. 1 (seq. ID No. 1) under low stringency conditions or a sequence complementary thereto and (b) is further characterized by its ability to cause a change in the pH of a culture of CHO cells when a MCH1 ligand is added to the culture and the CHO cells contain the nucleic acid which hybridized to the nucleic acid having the defined sequence or its complement. In one embodiment, the MCH1 receptor is a human MCH1 receptor.

In another embodiment, the MCH1 receptor is a rat MCH1 receptor. In another embodiment, the mammalian MCH1 receptor comprises substantially the same amino acid sequence as the sequence of the human MCH1 receptor encoded by plasmid pEXJ.HR-TL231. In a further embodiment, the mammalian MCH1 receptor comprises substantially the same amino acid sequence as that shown in FIG. 2 (Seq. ID No. 2). In another embodiment, the mammalian MCH1 receptor comprises the amino acid sequence shown in FIG. 2 (Seq. ID No. 2). In one embodiment, the compound is not previously known to bind to a mammalian MCH1 receptor. This invention further provides a compound identified by the above-described processes.

In one embodiment of the above-described processes, the cell is an insect cell. In another embodiment, the cell is a mammalian cell. In a further embodiment, the cell is nonneuronal in origin. In a further embodiment, the nonneuronal cell is a COS-7 cell, 293 human embryonic kidney cell, a CHO cell, a NIH-3T3cell, a mouse Y1 cell, or a LM(tk-) cell.

This invention provides a process involving competitive binding for identifying a chemical compound which specifically binds to a mammalian MCH1 receptor which comprises contacting cells expressing on their cell surface the mammalian MCH1 receptor, with both the chemical compound and a second chemical compound known to bind to the receptor, and separately with only the second chemical compound, under conditions suitable for binding of both compounds, and detecting specific binding of the chemical compound to the mammalian MCH1 receptor, a decrease in the binding of the second chemical compound to the mammalian MCH1 receptor in the presence of the chemical compound indicating that the chemical compound binds to the mammalian MCH1 receptor, wherein the cells do not normally express the mammalian MCH1 receptor and the DNA encoding the mammalian MCH1 receptor (a) hybridizes to a nucleic acid having the defined sequence shown in FIG. 1 (Seq. ID No. 1) under low stringency conditions or a sequence complementary thereto and (b) is further characterized by its ability to cause a change in the pH of a culture of CHO cells when a MCH1 ligand is added to the culture and the CHO cells contain the nucleic acid which hybridized to the nucleic acid having the defined sequence or its complement.

This invention also provides a process involving competitive binding for identifying a chemical compound which specifically binds to a mammalian MCH1 receptor which comprises contacting a membrane preparation from cells expressing on their cell surface the mammalian MCH1 receptor, with both the chemical compound and a second chemical compound known to bind to the receptor, and separately with only the second chemical compound, under conditions suitable for binding of both compounds, and detecting specific binding of the chemical compound to the mammalian MCH1 receptor, a decrease in the binding of the second chemical compound to the mammalian MCH1 receptor in the presence of the chemical compound indicating that the chemical compound binds to the mammalian MCH1 receptor, wherein the cells do not normally express the mammalian MCH1 receptor and the DNA encoding the mammalian MCH1 receptor (a) hybridizes to a nucleic acid having the defined sequence shown in FIG. 1 (Seq. ID No. 1) under low stringency conditions or a sequence complementary thereto and (b) is further characterized by its ability to cause a change in the pH of a culture of CHO cells when a MCH1 ligand is added to the culture and the CHO cells contain the nucleic acid which hybridized to the nucleic acid having the defined sequence or its complement.

In one embodiment, the mammalian MCH1 receptor is a human MCH1 receptor. In another embodiment, the mammalian MCH1 receptor is a rat MCH1 receptor. In another embodiment, the mammalian MCH1 receptor comprises substantially the same amino acid sequence as the human MCH1 receptor encoded by plasmid pEXJ.HRTL231. In a further embodiment, the mammalian MCH1 receptor comprises substantially the same amino acid sequence as that shown in FIG. 2 (Seq. I.D. No. 2). In another embodiment, the mammalian MCH1 receptor comprises the amino acid sequence shown in FIG. 2 (Seq. I.D. No. 2).

In one embodiment, the cell is an insect cell. In another embodiment, the cell is a mammalian cell. In a further embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk-) cell. In one embodiment, the compound is not previously known to bind to a mammalian MCH1 receptor.

This invention provides a compound identified by the above-described processes.

This invention provides a method of screening a plurality of chemical compounds not known to bind to a mammalian MCH1 receptor to identify a compound which specifically binds to the mammalian MCH1 receptor, which comprises (a) contacting cells transfected with and expressing DNA encoding the mammalian MCH1 receptor with the plurality of compounds not known to bind specifically to the mammalian MCH1 receptor, under conditions permitting binding of compounds known to bind the mammalian MCH1 receptor; (b) determining whether the binding of a compound known to bind to the mammalian MCH1 receptor is reduced in the presence of the compounds within the plurality of compounds, relative to the binding of the compound in the absence of the plurality of compounds; and if so (c) separately determining the binding to the mammalian MCH1 receptor of compounds included in the plurality of compounds, so as to thereby identify the compound which specifically binds to the mammalian MCH1 receptor.

This invention provides a method of screening a plurality of chemical compounds not known to bind to a mammalian MCH1 receptor to identify a compound which specifically binds to the mammalian MCH1 receptor, which comprises (a) contacting a membrane preparation from cells transfected with and expressing the mammalian MCH1 receptor with the plurality of compounds not known to bind specifically to the mammalian MCH1 receptor, under conditions permitting binding of compounds known to bind the mammalian MCH1 receptor; (b) determining whether the binding of a compound known to bind to the mammalian MCH1 receptor is reduced in the presence of the compounds within the plurality of compounds, relative to the binding of the compound in the absence of the plurality of compounds; and if so (c) separately determining the binding to the mammalian MCH1 receptor of compounds included in the plurality of compounds, so as to thereby identify the compound which specifically binds to the mammalian MCH1 receptor.

In one embodiment of the above-described methods, the mammalian MCH1 receptor is a human MCH1 receptor. In another embodiment, the mammalian MCH1 receptor is a rat MCH1 receptor. In another embodiment, the cell is a mammalian cell. In a further embodiment, the mammalian cell is non-neuronal in origin. In another embodiment, the non-neuronal cell is a COS-7 cell, a 293 human embryonic kidney cell, a LM(tk-) cell, a CHO cell, a mouse Y1 cell, or an NIH-3T3 cell.

This invention also provides a method of detecting expression of a mammalian MCH1 receptor by detecting the presence of mRNA coding for the mammalian MCH1 receptor which comprises obtaining total mRNA from the cell and contacting the mRNA so obtained from a nucleic acid probe under hybridizing conditions, detecting the presence of mRNA hybridizing to the probe, and thereby detecting the expression of the mammalian MCH1 receptor by the cell.

This invention further provides a method of detecting the presence of a mammalian MCH1 receptor on the surface of a cell which comprises contacting the cell with an antibody under conditions permitting binding of the antibody to the receptor, detecting the presence of the antibody bound to the cell, and thereby detecting the presence of the mammalian MCH1 receptor on the surface of the cell.

This invention provides a method of determining the physiological effects of varying levels of activity of human MCH1 receptors which comprises producing a transgenic, nonhuman mammal whose levels of human MCH1 receptor activity are varied by use of an inducible promoter which regulates human MCH1 receptor expression.

This invention also provides a method of determining the physiological effects of varying levels of activity of human MCH1 receptors which comprises producing a panel of transgenic, nonhuman mammals each expressing a different amount of human MCH1 receptor.

This invention provides a method for identifying an antagonist capable of alleviating an abnormality wherein the abnormality is alleviated by decreasing the activity of a human MCH1 receptor comprising administering a compound to a transgenic, nonhuman mammal, and determining whether the compound alleviates the physical and behavioral abnormalities displayed by the transgenic, nonhuman mammal as a result of overactivity of a human MCH1 receptor, the alleviation of the abnormality identifying the compound as an antagonist. This invention also provides an antagonist identified by the above-described method. This invention further provides a pharmaceutical composition comprising an antagonist identified by the abovedescribed method and a pharmaceutically acceptable carrier. This invention provides a method of treating an abnormality in a subject wherein the abnormality is alleviated by decreasing the activity of a human MCH1 receptor which comprises administering to the subject an effective amount of this pharmaceutical composition, thereby treating the abnormality.

This invention provides a method for identifying an agonist capable of alleviating an abnormality in a subject wherein the abnormality is alleviated by increasing the activity of a human MCH1 receptor comprising administering a compound to transgenic, nonhuman mammal, and determining whether the compound alleviates the physical and behavioral abnormalities displayed by the transgenic, nonhuman mammal, the alleviation of the abnormality identifying the compound as an agonist. This invention also provides an agonist identified by the above-described method. This invention further provides a pharmaceutical composition comprising an agonist identified by the above-described method and a pharmaceutically acceptable carrier. This invention further provides a method of treating an abnormality in a subject wherein the abnormality is alleviated by increasing the activity of a human MCH1 receptor which comprises administering to the subject an effective amount of this pharmaceutical composition, thereby treating the abnormality.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a human MCH1 receptor and labeled with a detectable marker; (e) detecting labeled bands which have hybridized to the DNA encoding a human MCH1 receptor labeled with a detectable marker to create a unique band pattern specific to the DNA of subjects suffering from the disorder; (f) preparing DNA obtained for diagnosis by steps (a)–(e); and (g) comparing the unique band pattern specific to the DNA of subjects suffering from the disorder from step (e) and the DNA obtained for diagnosis from step (f) to determine whether the patterns are the same or different and to diagnose thereby predisposition to the disorder if the patterns are the same. In one embodiment, a disorder associated with the activity of a specific mammalian allele is diagnosed.

This invention provides a method of preparing the purified human MCH1 receptor which comprises: (a) inducing cells to express the human MCH1 receptor; (b) recovering the human MCH1 receptor from the induced cells; and (c) purifying the human MCH1 receptor so recovered.

This invention provides a method of preparing the purified human MCH1 receptor which comprises: (a) inserting nucleic acid encoding the human MCH1 receptor in a suitable vector; (b) introducing the resulting vector in a suitable host cell; (c) placing the resulting cell in suitable condition permitting the production of the isolated human MCH1 receptor; (d) recovering the human MCH1 receptor produced by the resulting cell; and (e) purifying the human MCH1 receptor so recovered.

This invention provides a process for determining whether a chemical compound is a mammalian MCH1 receptor agonist which comprises contacting cells transfected with and expressing DNA encoding the mammalian MCH1 receptor with the compound under conditions permitting the activation of the mammalian MCH1 receptor, and detecting an increase in mammalian MCH1 receptor activity, so as to thereby determine whether the compound is a mammalian MCH1 receptor agonist. This invention also provides a process for determining whether a chemical compound is a mammalian MCH1 receptor antagonist which comprises contacting cells transfected with and expressing DNA encoding the mammalian MCH1 receptor with the compound in the presence of a known mammalian MCH1 receptor agonist, under conditions permitting the activation of the mammalian MCH1 receptor, and detecting a decrease in mammalian MCH1 receptor activity, so as to thereby determine whether the compound is a mammalian MCH1 receptor antagonist. In one embodiment, the mammalian MCH1 receptor is a human MCH1 receptor.

This invention further provides a pharmaceutical composition which comprises an amount of a mammalian MCH1 receptor agonist determined by the above-described process effective to increase activity of a mammalian MCH1 receptor and a pharmaceutically acceptable carrier. In one embodiment, the mammalian MCH1 receptor agonist is not previously known.

This invention provides a pharmaceutical composition which comprises an amount of a mammalian MCH1 receptor antagonist determined by the above-described process effective to reduce activity of a mammalian MCH1 receptor and a pharmaceutically acceptable carrier. In one embodiment, the mammalian MCH1 receptor antagonist is not previously known.

This invention provides a process for determining whether a chemical compound specifically binds to and activates a mammalian MCH1 receptor, which comprises contacting cells producing a second messenger response and expressing on their cell surface the mammalian MCH1 receptor, wherein such cells do not normally express the mammalian MCH1 receptor, with the chemical compound under conditions suitable for activation of the mammalian MCH1 receptor, and measuring the second messenger response in the presence and in the absence of the chemical compound, a change in the second messenger response in the presence of the chemical compound indicating that the compound activates the mammalian MCH1 receptor. In one embodiment, the second messenger response comprises chloride channel activation and the change in second messenger is an increase in the level of inward chloride current.

This invention also provides a process for determining whether a chemical compound specifically binds to and inhibits activation of a mammalian MCH1 receptor, which comprises separately contacting cells producing a second messenger response and expressing on their cell surface the mammalian MCH1 receptor, wherein such cells do not normally express the mammalian MCH1 receptor, with both the chemical compound and a second chemical compound known to activate the mammalian MCH1 receptor, and with only the second chemical compound, under conditions suitable for activation of the mammalian MCH1 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian MCH1 receptor. In one embodiment, the second messenger response comprises chloride channel activation and the change in second messenger response is a smaller increase in the level of inward chloride current in the presence of both the chemical compound and the second chemical compound than in the presence of only the second chemical compound. This invention also provides the above-described processes performed with membrane preparations from cells producing a second messenger response and transfected with and expressing the mammalian MCH1 receptor.

In one embodiment of the above-described processes, the mammalian MCH1 receptor is a human MCH1 receptor. In another embodiment, the mammalian MCH1 receptor is a rat MCH1 receptor. In another embodiment, the mammalian MCH1 receptor comprises substantially the same amino acid sequence as encoded by the plasmid pEXJ.HR-TL231. In a further embodiment, the mammalian MCH1 receptor comprises substantially the same amino acid sequence as that shown in FIG. 2 (Seq. I.D. No. 2). In another embodiment, the mammalian MCH1 receptor comprises an amino acid sequence as shown in FIG. 2 (Seq. I.D. No. 2). In an embodiment, the cell is an insect cell. In a further embodiment, the cell is a mammalian cell. In a still further embodiment, the mammalian cell is nonneuronal in origin. In another embodiment, the nonneuronal cell is a COS-7 cell, CHO cell, 293 human embryonic kidney cell, NIH-3T3 cell or LM(tk-) cell. In an embodiment, the compound is not previously known to bind to a mammalian MCH1 receptor. This invention also provides a compound determined by the above-described processes.

This invention also provides a pharmaceutical composition which comprises an amount of a mammalian MCH1 receptor agonist determined by the above-described processes effective to increase activity of a mammalian MCH1 receptor and a pharmaceutically acceptable carrier. In one embodiment, the mammalian MCH1 receptor agonist is not previously known.

This invention further provides a pharmaceutical composition which comprises an amount of a mammalian MCH1 receptor antagonist determined by the above-described processes effective to reduce activity of a mammalian MCH1 receptor and a pharmaceutically acceptable carrier. In one embodiment, the mammalian MCH1 receptor antagonist is not previously known.

This invention provides a method of screening a plurality of chemical compounds not known to activate a mammalian MCH1 receptor to identify a compound which activates the mammalian MCH1 receptor which comprises: (a) contacting cells transfected with and expressing the mammalian MCH1 receptor with the plurality of compounds not known to activate the mammalian MCH1 receptor, under conditions permitting activation of the mammalian MCH1 receptor; (b) determining whether the activity of the mammalian MCH1 receptor is increased in the presence of the compounds; and if so (c) separately determining whether the activation of the mammalian MCH1 receptor is increased by each compound included in the plurality of compounds, so as to thereby identify the compound which activates the mammalian MCH1 receptor. In one embodiment, the mammalian MCH1 receptor is a human MCH1 receptor. In another embodiment, the mammalian MCH1 receptor is a rat MCH1 receptor.

This invention provides a method of screening a plurality of chemical compounds not known to inhibit the activation of a mammalian MCH1 receptor to identify a compound which inhibits the activation of the mammalian MCH1 receptor, which comprises: (a) contacting cells transfected with and expressing the mammalian MCH1 receptor with the plurality of compounds in the presence of a known mammalian MCH1 receptor agonist, under conditions permitting activation of the mammalian MCH1 receptor; (b) determining whether the activation of the mammalian MCH1 receptor is reduced in the presence of the plurality of compounds, relative to the activation of the mammalian MCH1 receptor in the absence of the plurality of compounds; and if so (c) separately determining the inhibition of activation of the mammalian MCH1 receptor for each compound included in the plurality of compounds, so as to thereby identify the compound which inhibits the activation of the mammalian MCH1 receptor. In one embodiment, the mammalian MCH1 receptor is a human MCH1 receptor. In another embodiment, the mammalian MCH1 receptor is a rat MCH1 receptor.

In one embodiment of the above-described methods, the cell is a mammalian cell. In another embodiment, the mammalian cell is non-neuronal in origin. In a further embodiment, the non-neuronal cell is a COS-7 cell, a 293 human embryonic kidney cell, a LM(tk-) cell or an NIH-3T3 cell.

This invention provides a pharmaceutical composition comprising a compound identified by the above-described methods effective to increase mammalian MCH1 receptor activity and a pharmaceutically acceptable carrier.

This invention also provides a pharmaceutical composition comprising a compound identified by the above-described methods effective to decrease mammalian MCH1 receptor activity and a pharmaceutically acceptable carrier.

This invention further provides a method of measuring receptor activation in an oocyte expression system such as a Xenopus oocyte expression system or melanophore. In an embodiment, receptor activation is determined by measurement of ion channel activity. In another embodiment, receptor activation is measured by aequorin luminescence.

Expression of genes in Xenopus oocytes is well known in the art (Coleman, A., 1984; Masu, Y.,et al., 1994) and is performed using microinjection of native mRNA or in vitro synthesized mRNA into frog oocytes. The preparation of in vitro synthesized mRNA can be performed by various standard techniques (Sambrook, et al. 1989) including using T7 polymerase with the mCAP RNA mapping kit (Stratagene).

This invention provides a method of treating an abnormality in a subject wherein the abnormality is alleviated by increasing the activity of a mammalian MCH1 receptor which comprises administering to the subject an amount of a compound which is a mammalian MCH1 receptor agonist effective to treat the abnormality. In separate embodiments, the abnormality is a regulation of a steroid or pituitary hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, a sensory modulation and transmission disorder, a motor coordination disorder, a sensory integration disorder, a motor integration disorder, a dopaminergic function disorder, a sensory transmission disorder, an olfaction disorder, a sympathetic innervation disorder, an affective disorder, a stress-related disorder, a fluid-balance disorder, a seizure disorder, pain, psychotic behavior, morphine tolerance, opiate addiction or migraine.

This invention provides a method of treating an abnormality in a subject wherein the abnormality is alleviated by decreasing the activity of a mammalian MCH1 receptor which comprises administering to the subject an amount of a compound which is a mammalian MCH1 receptor antagonist effective to treat the abnormality. In separate embodiments, the abnormality is a regulation of a steroid or pituitary hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, a sensory modulation and transmission disorder, a motor coordination disorder, a sensory integration disorder, a motor integration disorder, a dopaminergic function disorder, a sensory transmission disorder, an olfaction disorder, a sympathetic innervation disorder, an affective disorder, a stress-related disorder, a fluid-balance disorder, a seizure disorder, pain, psychotic behavior, morphine tolerance, opiate addiction or migraine.

This invention provides a process for making a composition of matter which specifically binds to a mammalian MCH1 receptor which comprises identifying a chemical compound using any of the processes described herein for identifying a compound which binds to and/or activates or inhibits activation of a mammalian MCH1 receptor and then synthesizing the chemical compound or a novel structural and functional analog or homolog thereof. In one embodiment, the mammalian MCH1 receptor is a human MCH1 receptor. In another embodiment, the mammalian MCH1 receptor is a rat MCH1 receptor.

This invention further provides a process for preparing a pharmaceutical composition which comprises admixing a pharmaceutically acceptable carrier and a therapeutically effective amount of a chemical compound identified by any of the processes described herein for identifying a compound which binds to and/or activates or inhibits activation of a mammalian MCH1 receptor or a novel structural and functional analog or homolog thereof. In one embodiment, the mammalian MCH1 receptor is a human MCH1 receptor. In another embodiment, the mammalian MCH1 receptor is a rat MCH1 receptor.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Cloning of Human MCH1 Receptor

Discovery of an Expressed Sequence Tag (EST) F07228 in GENEMEL Homologous to FB41a A BLAST search of GENEMBL was performed with the GCG sequence analysis package (Genetics Computer Group, Madison, Wis.) using a Synaptic Pharmaceutical Corporation proprietary sequence, FB41a, as a query. This resulted in the identification of an EST (accession number F07228) with a high degree of homology to FB41a and somatostatin, opiate and galanin receptors.

Construction and Screening of a Human Hippocampal cDNA Library

Poly A+ RNA was purified from human hippocampal RNA (Clontech) using a FastTrack kit (Invitrogen, Corp.). DS– cDNA was synthesized from poly A+ RNA according to Gubler and Hoffman (1983) with minor modifications. The resulting cDNA was ligated to BstXI adaptors (Invitrogen, Corp.) and the excess adaptors removed by exclusion column chromatography. High molecular weight fractions of size-selected ds-cDNA were ligated in pEXJ.BS, an Okayama and Berg expression vector modified from pcEXV (Miller and Germain, 1986) to contain BstXI and other additional restriction sites. A total of $2.2 \times 10^6$ independent clones with a mean insert size of 3.0 kb were generated. The library was plated on agar plates (ampicillin selection) and glycerol stocks for 450 pools of 5000 independent clones were prepared. Primary glycerol stocks were also grouped together in groups of approximately 10 to create superpools.

Cloning of the Full-Length Sequence of MCH1

Glycerol stocks of the superpools and primary pools from the human hippocampal cDNA library were screened by PCR with F07228 specific primers T579 and T580 using Taq DNA Polymerase (Boehringer-Mannheim, Indianapolis, Ind.) and the following PCR protocol: 94° C. hold for 5 minutes; 40 cycles of 94° C. for 2 minute, 68° C. for 4 minutes; 7 minute hold at 68° C.; 4° C. hold until the samples are run on a gel. One positive primary pool 490, was successively divided into subpools, amplified in LB medium overnight and screened by PCR using primers T579 and T580. One positive subpool, 490-4-10-23 was plated on agar plates (ampicillin selection), and colonies were transferred to nitrocellulose membranes (Schleicher and Schuell, Keene, N.H.). Filters were hybridized for two days under high stringency conditions with $10^6$ cpm/ml of a $^{32}$P-labeled cDNA probe, T581, designed against the F07228 EST sequence. Filters were washed and apposed to Biomax MS film (Kodak). Seven positive colonies were picked, streaked on LB-AMP plates, and grown overnight. Two individual colonies from each of the original seven were picked and subjected to vector-anchored PCR using the following primer pairs: T95, T580 and T94, T579. One positive colony, G1, was amplified overnight in TB and processed for plasmid purification. This plasmid was designated TL230 and sequenced on both strands with a Sequence kit (US Biochemical, Cleveland, Ohio). Nucleotide and peptide sequence analysis were performed with GCG programs (Genetics Computer Group, Madison, Wis.). A HindIII—KpnI fragment of TL230 was subcloned into the mammalian expression vector pEXJ, and named TL231.

Primers and Probes:

TL579: 5'-GGGAACTCCACGGTCATCTTCGCGGT-3' (Seq. I.D. No. 5)

TL580: 5'-TAGCGGTCAATGGCCATGGCGGTCAG-3' (Seq. I.D. No. 6)

T L 5 8 1 : 5'-CTCCTGGGCATGCCCTTCATGATCCACCAGCT CATGGGCAATGGG-3' (Seq. I.D. No. 7)

TL94: 5'-CTTCTAGGCCTGTACGGAAGTGTTA-3' (Seq. I.D. No. 8)

TL95: 5'-GTTGTGGTTTGTCCAAACTCATCAATG-3' (Seq. I.D. No. 9)

Isolation of a Fragment of a Species Homologue of TL231 (Human MCH1)

To obtain a fragment of a species homologue of TL231, the species genomic DNA (Clontech) may be amplified with a forward PCR primer corresponding to one of the TM regions of TL231 and a reverse primer corresponding to another TM region of TL231. PCR may be performed with the Expand Long Template PCR System (Boeringer Mannheim), for example, under the following conditions: 30 sec at 94° C., 1.5 min at 50° C., 1.5 min at 68° C. for 40 cycles, with a pre- and post-incubation of 5 min at 94° C. and 7 min at 68° C., respectively. A band is isolated, subcloned using the TA cloning kit (Invitrogen), and sequenced. The sequence is run and analyzed on an ABI PRISM 377 BigDye Terminator Cycle Sequencing Kit Sequencer. Forward and reverse PCR primers are designed against this sequence and used to amplify a band from genomic DNA using, for example, the following conditions: 30 sec at 94° C., 1.5 min at 68° C. for 35 cycles, with a pre- and post-incubation of 5 min at 94° C. and 5 min at 68° C., respectively. The PCR product is subcloned using the TA cloning kit (Invitrogen). Miniprep cultures of transformants are prepared and sequenced as above.

Isolation of a Full-Length Species Homolog of TL231 (Human MCH1)

A nucleic acid sequence encoding an MCH1 receptor may be isolated using standard molecular biology techniques and approaches such as those briefly described below:

Approach #1: To obtain a full-length MCH1 receptor, a cosmid library could be screened with a $^{32}$P-labeled oligonucleotide probe.

The full-length sequence may be obtained by sequencing this cosmid clone with additional sequencing primers. Since one intron is present in this gene the full-length intronless gene may be obtained from cDNA using standard molecular biology techniques. For example, a forward PCR primer designed in the 5'UT and a reverse PCR primer designed in the 3'UT may be used to amplify a full-length, intronless gene from cDNA. Standard molecular biology techniques could be used to subclone this gene into a mammalian expression vector.

Approach #2: Standard molecular biology techniques could be used to screen commercial cDNA phage libraries by hybridization under high stringency with a $^3$P-labeled oligonucleotide probe. One may isolate a fulllength MCH1 receptor by obtaining a plaque purified clone from the lambda libraries and then subjecting the clone to direct DNA sequencing. Alternatively, standard molecular biology techniques could be used to screen in-house cDNA plasmid libraries by PCR amplification of library pools using primers to the MCH1 sequence. A full-length clone could be isolated by Southern hybridization of colony lifts of positive pools with a $^{32}$-P-labeled oligonucleotide probe.

Approach #3: As yet another alternative method, one could utilize 3' and 5' RACE to generate PCR products from cDNA expressing MCH1 which contain the additional sequences of MCH1. These RACE PCR products could then be sequenced to determine the missing sequence. This new sequence could then be used to design a forward PCR primer in the 5'UT and a reverse primer in the 3'UT. These primers could then be used to amplify a full-length MCH1 clone from cDNA.

Host Cells

A broad variety of host cells can be used to study heterologously expressed proteins. These cells include but are not restricted to assorted mammalian lines such as; Cos-7, CHO, LM(tk-), HEK293, etc.; insect cell lines such as; Sf9, Sf21, etc.; amphibian cells such as xenopus oocytes; and others.

COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells are trypsinized and split 1:6 every 3–4 days.

Human embryonic kidney 293 cells are grown on 150 mm plates in DMEM with supplements (10% bovine calf serum, 4 mM glutamine, 100 units/ml penicillin/100 µg/ml streptomycin) at 37° C., 5% $CO_2$. Stock plates of 293 cells are trypsinized and split 1:6 every 3–4 days.

Mouse fibroblast LM(tk-) cells are grown on 150 mm plates in D-MEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of LM(tk-) cells are trypsinized and split 1:10 every 3–4 days.

Chinese hamster ovary (CHO) cells were grown on 150 mm plates in HAM's F-12 medium with supplements (10% bovine calf serum, 4 mM L-glutamine and 100 units/ml penicillin/ 100 µg/ml streptomycin) at 37° C., 5% $CO_2$. Stock plates of CHO cells are trypsinized and split 1:8 every 3–4 days.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/ml penicillin/100 µg/ml streptomycin) at 37° C., 5% $CO_2$. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

In some cases, cell lines that grow as adherent monolayers can be converted to suspension culture to increase cell yield and provide large batches of uniform assay material for routine receptor screening projects.

Xenopus oocytes can also be used as a host system for transient expression of heterologous proteins. Their maintenance and usage is described in the electrophysiological methods section that follows.

Transient Expression

DNA encoding proteins to be studied can be transiently expressed in a variety of mammalian, insect, amphibian and other cell lines by several methods including but not restricted to; calcium phosphate-mediated, DEAE-dextran mediated, Liposomal-mediated, viral-mediated, electroporation-mediated and microinjection delivery. Each of these methods may require optimization of assorted experimental parameters depending on the DNA, cell line, and the type of assay to be subsequently employed.

A typical protocol for the calcium phosphate method as applied to LM(tk-) cells is described as follows; Adherent cells are harvested approximately twenty-four hours before transfection and replated at a density of 1–2×10$^5$ cells/cm$^2$ in a 100 mm tissue culture dish and allowed to incubate over night at 37° C. at 5% $CO_2$. 250 µl of a mixture of $CaCl_2$ and DNA (20 µg DNA in 250 mM $CaCl_2$) is added to a 5 ml plastic tube and 250 ul of 2×HBS (250 mM NaCl, 10 mM KCl, 1.5 mM $Na_2HPO_4$, 12 mM dextrose, 50 mM HEPES) is slowly added with gentle mixing. The mixture is allowed to incubate for 20 minutes at room temperature to allow a DNA precipitate to form. The cells are then washed with complete medium, 10 ml of culture medium is added to each plate, followed by addition of the DNA precipitate. The cells are then incubated for 24 to 48 hours at 37° C. at 5% $CO_2$.

A typical protocol for the DEAE-dextran method as applied to Cos-7 cells is described as follows; Cells to be used for transfection are split 24 hours prior to the transfection to provide flasks which are 70–80% confluent at the time of transfection. Briefly, 8 µg of receptor DNA plus 8 µg of any additional DNA needed (e.g. $G_\alpha$ protein expression vector, reporter construct, antibiotic resistance marker, mock vector, etc.) are added to 9 ml of complete DMEM plus DEAE-dextran mixture (10 mg/ml in PBS). Cos-7 cells plated into a T225 flask (sub-confluent) are washed once with PBS and the DNA mixture is added to each flask. The cells are allowed to incubate for 30 minutes at 37° C., 5% $CO_2$. Following the incubation, 36 ml of complete DMEM with 80 µM chloroquine is added to each flask and allowed to incubate an additional 3 hours. The medium is then aspirated and 24 ml of complete medium containing 10% DMSO for exactly 2 minutes and then aspirated. The cells are then washed 2 times with PBS and 30 ml of complete DMEM added to each flask. The cells are then allowed to incubate over night. The next day the cells are harvested by trypsinization and reseeded as needed depending upon the type of assay to be performed.

A typical protocol for liposomal-mediated transfection as applied to CHO cells is described as follows; Cells to be used for transfection are split 24 hours prior to the transfection to provide flasks which are 70–80% confluent at the time of transfection. A total of 10 µg of DNA which may include varying ratios of receptor DNA plus any additional DNA needed (e.g. $G_\alpha$ protein expression vector, reporter construct, antibiotic resistance marker, mock vector, etc.) is used to transfect each 75 cm flask of cells. Liposomal mediated transfection is carried out according to the manufacturer's recommendations (LipofectAMINE, GibcoBRL, Bethesda, Md.). Transfected cells are harvested 24 h post transfection and used or reseeded according the requirements of the assay to be employed.

A typical protocol for the electroporation method as applied to Cos-7 cells is described as follows; Cells to be used for transfection are split 24 hours prior to the transfection to provide flasks which are subconfluent at the time of transfection. The cells are harvested by trypsinization resuspended in their growth media and counted. 4×10$^6$ cells are suspended in 300 µl of DMEM and placed into an electroporation cuvette. 8 µg of receptor DNA plus 8 µg of any additional DNA needed (e.g. $G_\alpha$ protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 µF capacitance). Following the pulse, 800 µl of complete DMEM is added to each cuvette and the suspension transferred to a sterile tube. Complete medium is added to each tube to bring the final cell concentration to 1×10$^5$ cells/100 µl. The cells are then plated as needed depending upon the type of assay to be performed.

A typical protocol for viral mediated expression of heterolgous proteins is described as follows for baculovirus infection of insect Sf9 cells. The coding region of DNA encoding the receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×10$^6$ *Spodoptera frugiperda* insect Sf9 cells by the calcium phosphate co-precipitation method, as outlined in by Pharmingen (in "Baculovirus Expression Vector System: Procedures and Methods Manual"). The cells then are incubated for 5 days at 27° C. The supernatant of the co-transfection plate may be collected by centrifugation and the recombinant virus plaque purified. The procedure to infect cells with virus, to prepare stocks of virus and to titer the virus stocks are as described in Pharmingen's manual. Similar principals would in general apply to mammalian cell expression via retro-viruses, Simliki forest virus and double stranded DNA viruses such as adeno-, herpes-, and vacinia-viruses, and the like.

Microinjection of cRNA encoding for proteins of interest is useful for the study of protein function in xenopus oocytes as well as cultured mammalian cells. A typical protocol for the preparation of cRNA and injection into xenopus oocytes can be found in the following electrophysiology section.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the heterologous DNA. An assortment of resistance genes are available including but not restricted to Neomycin, Kanamycin, and Hygromycin. For the purposes of receptor studies, stable expression of a heterologous receptor protein is carried out in, but not necessarily restricted to, mammalian cells including, CHO, HEK293, LM(tk-), etc.

Cell Membrane Preparation

For binding assays, pellets of transfected cells are suspended in ice-cold buffer (20 mM Tris.HCl, 5 mM EDTA, pH 7.4) and homogenized by sonication for 7 sec. The cell lysates are centrifuged at 200×g for 5 min at 4° C. The supernatants are then centrifuged at 40,000×g for 20 min at 4° C. The resulting pellets are washed once in the homogenization buffer and suspended in binding buffer (see methods for radioligand binding). Protein concentrations are determined by the method of Bradford (1976) using bovine serum albumin as the standard. Binding assays are usually performed immediately, however it is possible to prepare membranes in batch and store frozen in liquid nitrogen for future use.

Radioligand Binding Assays

Cells may be screened for the presence of endogenous human receptor by radioligand binding (described in detail below). Cells with either no or a low level of the endogenous human receptor disclosed herein may be transfected with the exogenous receptor.

MCH1 binding experiments with membranes (20–40 μg membrane protein) from transfected cells are performed with 0.1 nM [$^{125}$I]Phe$^{13}$-Tyr$^{19}$-MCH (Custom labeled by NEN) using incubation buffer consisting of 50 mM Tris pH 7.4, 10 mM MgCl$_2$, 2 μg/ml aprotonin, 0.5 mM PMSF and 50 μg/ml bacitracin. Binding is performed at 25° C. for 1 hr. Incubations are terminated by rapid vacuum filtration over GF/C glass fiber filters, presoaked in 5 PEI using 50 mM Tris pH 7.4 containing 0.01% triton X-100 as wash buffer. In all experiments nonspecific binding is defined using 10 μM unlabeled MCH.

Functional Assays

Cells may be screened for the presence of endogenous mammalian receptor using functional assays (described in detail below). Cells with no or a low level of endogenous receptor present may be transfected with the exogenous receptor for use in the following functional assays.

A wide spectrum of assays can be employed to screen for receptor activation. These range from traditional measurements of phosphatidyl inositol, cAMP, $Ca^{++}$, and $K^+$, for example; to systems measuring these same second messengers but which have been modified or adapted to be higher throughput, more generic, and more sensitive; to cell based platforms reporting more general cellular events resulting from receptor activation such as metabolic changes, differentiation, and cell division/proliferation, for example; to high level organism assays which monitor complex physiological or behavioral changes thought to be involved with receptor activation including cardiovascular, analgesic, orexigenic, anxiolytic, and sedation effects, for example.

Cyclic AMP (cAMP) Assay

The receptor-mediated stimulation or inhibition of cyclic AMP (cAMP) formation may be assayed in cells expressing the mammalian receptors. Cells are plated in 96-well plates and incubated in Dulbecco's phosphate buffered saline (PBS) supplemented with 10 mM HEPES, 1 mM isobutyl-methylxanthine for 20 min at 37° C., in 5% $CO_2$. Test compounds are added with or without 10 μM forskolin and incubated for an additional 10 min at 37° C. The medium is then aspirated and the reaction stopped by the addition of 100 mM HCl. The plates are stored at 4° C. for 15 min, and the cAMP content in the stopping solution measured by radioimmunoassay. Radioactivity may be quantified using a gamma counter equipped with data reduction software.

Arachidonic acid Release Assay

Cells expressing the mammalian receptor are seeded into 96 well plates and grown for 3 days in HAM's F-12 with supplements. [$^3$H]-arachidonic acid (specific activity=0.75 μCi/ml) is delivered as a 100 μL aliquot to each well and samples were incubated at 37° C., 5% $CO_2$. for 18 hours. The labeled cells are washed three times with 200 μL HAM's F-12. The wells are then filled with medium (200 μL) and the assay is initiated with the addition of peptides or buffer (22 μL). Cells are incubated for 30 min at 37° C., 5% $CO_2$. Supernatants are transferred to a microtiter plate and evaporated to dryness at 75° C. in a vacuum oven. Samples are then dissolved and resuspended in 25 μL distilled water. Scintillant (300 μL) is added to each well and samples are counted for $^3$H in a Trilux plate reader. Data are analyzed using nonlinear regression and statistical techniques available in the GraphPAD Prism package (San Diego, Calif.).

Intracellular Calcium Mobilization Assay

The intracellular free calcium concentration may be measured by microspectroflourometry using the fluorescent indicator dye Fura-2/AM (Bush et al, 1991). Cells are seeded onto a 35 mm culture dish containing a glass coverslip insert, washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Inositol Phosphate Assay

Guidelines for cell preparation and assay of the second messenger inositol phosphate (IP) are described below for a typical protocol involving transiently transfected Cos-7 cells; For a 96 well microplate format assay, cells are plated at 70,000 cells per well and allowed to incubate for 24 hours after the transfection procedure. The cells are then labeled with 0.5 μCi [$^3$H]myo-inositol per micro-well over night at 37° C., 5% $CO_2$. Immediately before the assay, the medium is removed and replaced with 90 μl PBS containing 10 mM LiCl. The plates are then incubated for 15 minutes at 37° C., 5% $CO_2$. Following the incubation, the transfectants are challenged with agonist (10 μi/well; 10× concentration) for 30 minutes at 37° C., 5% $CO_2$. The challenge is terminated and the cells lysed by the addition of 100 μl cold 5% v/v trichloroacetic acid (TCA), followed by an incubation at 4° C. for greater than 30 minutes. Total IPs are isolated from the lysate by ion exchanae chromatography. Briefly, the lysed contents of the wells are transferred to a Multiscreen HV filter plate (Millipore) containing 100 μl Dowex AG1-X8 suspension (50% v/v, water:resin) (200–400 mesh, formate form). The filter plates are placed on a vacuum manifold to wash and elute the resin bed. Each well is first washed 2 times with 200 μl 5 mM myoinositol. Total [$^3$H]IPs are eluted with 75 μl of 1.2 M ammonium formate/0.1 M formic acid into Wallac 96-well plates. 200 μl of SuperMix scintillation cocktail is added to each well, mixed well, allowed to equilibrate and counted on a Micro Beta Trilux scintillation counter. (Note: The assay may be scaled to a 24 well format by simple adjustment of reagent volumes and employing individual chromatographic columns.)

GTPγS Functional Assay

Membranes from cells transfected with the mammalian receptors are suspended in assay buffer (50 mM Tris, 100 mM NaCl, 5 mM $MgCl_2$, pH 7.4) supplemented with 0.2% BSA and 10 μM GDP. Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus GTPγS (final concentration=100 μM). Final membrane protein concentration≈90 μg/ml. Samples are incubated in the presence or absence of MCH (final concentration=1 μM) for 30 min. at room temperature, then filtered on a Millipore vacuum manifold and washed three times with cold assay buffer. Samples collected in the filter plate are treated with scintillant and counted for $^{35}$S in a Trilux (Wallac) liquid scintillation counter. It is expected that optimal results are obtained when the mammalian receptor membrane preparation is derived from an appropriately engineered heterologous expression system, i.e., an expression system resulting in high levels of expression of the mammalian receptor and/or expressing G-proteins having high turnover rates (for the exchange of GDP for GTP). GTPγS assays are well-known in the art, and it is expected that variations on the method described above, such as are described by e.g., Tian et al. (1994) or Lazareno and Birdsall (1993), may be used by one of ordinary skill in the art.

Transcription Assay

Guidelines for cell preparation and assay of receptor mediated transcription of Cos-7 cells transiently transfected by the DEAE-dextran method in a 96 microwell format is as follows; The c-fos-β-gal promoter/reporter construct used for these studies consists of the cfos promoter region (−384 to +19) (Schilling et al 1991, Yalkinoglu et al, 1995) inserted upstream of β-galactosidase cDNA containing expression vector pNASSβ (Clontech). Transcription activity is measured by assay of β-galactosidase enzyme activity as detected in a calorimetric assay. Forty-eight hours following transient transfection, the medium is removed and replaced with medium containing drug (e.g. MCH) typically at a concentration of 10 μM. The cells are allowed to incubate at 37° C., 5% $CO_2$ for at least 18 hours, after which the medium is aspirated and the cells washed with 200 μl PBS/well. The cells are then lysed with 100 μl AB buffer (100 mM Sodium Phosphate buffer, pH 8.0, 2 mM $MgSO_4$, 0.1 mM $MnCl_2$) for 10 minutes at room temperature. 100 μl of AB/Tx/β-mercaptoethanol (AB buffer with 0.5% Triton X-100, 40 mM β-mercaptoethanol) is then added to each well and the lysate allowed to incubate an additional 10 minutes at room temperature. The enzymatic color reaction is initiated by the addition of the substrate, ONPG/AB (4 mg/ml O-nitrophenyl-b-D-galactopyranoside in AB buffer). The reaction is allowed to proceed for 30 minutes or until yellow color becomes evident. Measurement of optical density is taken at 405 nm using a Dynatech microplate reader.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (Gq and G11) produce diacylglycerol (DAG) ase a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the mitogen and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the mitogen and a soluble extract is prepared. The extract is incubated at 30° C. for 10 min with gamma-32-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81chromatography paper, which retains the phosphorylated protein. The chromatography paper is washed and counted for $^{32}$P in a liquid scintillation counter. Alternatively, the cell extract is incubated with gamma-32-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then be aspirated through the filter, which retains the phosphorylated myelin basic protein. The filter is washed and counted for $^{32}$P by liquid scintillation counting.

Cell Proliferation Assay

Activation of a G protein coupled receptor may lead to a mitogenic or proliferative response which can be monitored via [$^3$H]-thymidine uptake. When cultured cells are incubated with [$^3$H]-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with [$^3$H]-thymidine at specific activities ranging from 1 to 10 $\mu$Ci/ml for 2–6 hrs. Harvesting procedures may involve trypsinization and trapping of cells by filtration over GF/C filters with or without a prior incubation in TCA to extract soluble thymidine. The filters are processed with scintillant and counted for H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Methods for Recording Currents in Xenopus Oocytes

Female *Xenopus laevis* (Xenopus-1, Ann Arbor, Mich.) are anesthetized in 0.2% tricain (3-aminobenzoic acid ethyl ester, Sigma Chemical Corp.) and a portion of ovary is removed using aseptic technique (Quick and Lester, 1994). Oocytes are defolliculated using 2 mg/ml collagenase (Worthington Biochemical Corp., Freehold, N.J.) in a solution containing 87.5 mM NaCl, 2 mM KCl, 2 mM MgCl$_2$ and 5 mM HEPES, pH 7.5. Oocytes may be injected (Nanoject, Drummond Scientific, Broomall, Pa.) with mammalian mRNA. Other oocytes may be injected with a mixture of mammalian mRNA and mRNA encoding the genes for G-protein-activated inward rectifiers (GIRK1 and GIRK4, U.S. Pat. Nos. 5,734,021 and 5,728,535). Genes encoding G-protein inwardly rectifying K$^{30}$ (GIRK) channels 1 and 4 (GIRK1 and GIRK4) were obtained by PCR using the published sequences (Kubo et al., 1993; Dascal et al., 1993; Krapivinsky et al., 1995and 1995b) to derive appropriate 5' and 3' primers. Human heart cDNA was used as template together with the primers 5'-CGCGGATCCATTATGTCTGCACTCCGAAGGA AATTTG-3' (Seq. I.D. No. 10) and 5'-CGCGAATTCTTATGTGAAGCGATCAGAGTTC ATTTTTC-3' (Seq. I.D. No. 11) for GIRK1 and 5'-GCGGGATCCGCTATGGCTGGTGATTCTAGG AATG-3' (Seq. I.D. No. 12) and 5'-CCGGAATTCCCCTCACACCGAGCCCCTGG-3' (Seq. I.D. No. 13) for GIRK4.

In each primer pair, the upstream primer contained a BamHI site and the downstream primer contained an EcoRI site to facilitate cloning of the PCR product into pcDNA1-Amp (Invitrogen). The transcription template for the mammalian receptor may be similarly obtained. mRNAs are prepared from separate DNA plasmids containing the complete coding regions of the mammalian receptor, GIRK1, and GIRK4. Plasmids are linearized and transcribed using the T7 polymerase ("Message Machine", Ambion). Alternatively, mRNA may be translated from a template generated by PCR, incorporating a T7 promoter and a poly A$^+$ tail. Each oocyte receives 2 ng each of GIRK1 and GIRK4 mRNA in combination with 25 ng of mammalian receptor mRNA. After injection of mRNA, oocytes are incubated at 16° C. on a rotating platform for 3–8 days. Dual electrode voltage clamp ("GeneClamp", Axon Instruments Inc., Foster City, Calif.) is performed using 3 M KCl-filled glass microelectrodes having resistances of 1–3 Mohms. Unless otherwise specified, oocytes are voltage clamped at a holding potential of –80 mV. During recordings, oocytes are bathed in continuously flowing (2–5 ml/min) medium containing 96 mM NaCl, 2 mM KCl, 2 mM CaCl$_2$, 2 mM MgCl$_2$, and 5 mM HEPES, pH 7.5 ("ND96"), or, in the case of oocytes expressing GIRK1 and GIRK4, elevated K$^+$ containing 96 mM KCl, 2 mM NaCl, 2 mM CaCl$_2$, 2 mM MgCl, and 5 mM HEPES, pH 7.5 ("hK") Drugs are applied by switching from a series of gravity fed perfusion lines.

Heterologous expression of GPCRs in Xenopus oocytes has been widely used to determine the identity of signaling pathways activated by agonist stimulation (Gundersen et al., 1983; Takahashi et al., 1987). Activation of the phospholipase C (PLC) pathway is assayed by applying test compound in ND96 solution to oocytes previously injected with mRNA for the mammalian receptor and observing inward currents at a holding potential of –80 mV. The appearance of currents that reverse at –25 mV and display other properties of the Ca$^{++}$-activated Cl$^-$ (chloride) channel is indicative of mammalian receptor-activation of PLC and release of IP3 and intracellular Ca$^{++}$. Such activity is exhibited by GPCRs that couple to G$_q$.

Measurement of inwardly rectifying K$^+$ (potassium) channel (GIRK) activity is monitored in oocytes that have been co-injected with mRNAs encoding the mammalian receptor, GIRK1, and GIRK4. The two GIRK gene products co-assemble to form a G-protein activated potassium channel known to be activated (i.e., stimulated) by a number of GPCRs that couple to G$_i$ or G$_o$ (Kubo et al., 1993; Dascal et al., 1993). Oocytes expressing the mammalian receptor plus the two GIRK subunits are tested for test compound responsivity by measuring K$^-$ currents in elevated K$^-$ solution (hK). Activation of inwardly rectifying currents that are sensitive to 30° $\mu$M Ba$^{++}$ signifies the mammalian receptor coupling to a G$_i$ or G$_o$ pathway in the oocytes.

Receptor/G Protein Co-Transfection Studies

A strategy for determining whether MCH1 can couple preferentially to selected G proteins involves co-transfection of MCH1 receptor cDNA into a host cell together with the cDNA for a G protein alpha sub-unit. Examples of G alpha sub-units include members of the G$\alpha$i/G$\alpha$o class (including G$\alpha$t2 and G$\alpha$z), the G$\alpha$q class, the G$\alpha$s class, and the G$\alpha$12/13 class. A typical procedure involves transient transfection into a host cell such as COS-7. Other host cells may be used. A key consideration is whether the cell has a downstream effector (a particular adenylate cyclase, phospholipase C, or channel isoform, for example) to support a functional response through the G protein under investigation. G protein beta gamma sub-units native to the cell are presumed to complete the G protein heterotrimer; otherwise specific beta and gamma sub-units may be co-transfected as well. Additionally, any individual or combination of alpha, beta, or gamma subunits may be co-transfected to optimize the functional signal mediated by the receptor.

The receptor/G alpha co-transfected cells are evaluated in a binding assay, in which case the radioligand binding. may be enhanced by the presence of the optimal G protein coupling or in a functional assay designed to test the receptor/G protein hypothesis. In one example, the MCH1 receptor may be hypothesized to inhibit cAMP accumulation through coupling with G alpha sub-units of the G$\alpha$i/G$\alpha$o class. Host cells co-transfected with the MCH1 receptor and appropriate G alpha sub-unit cDNA are stimulated with forskolin +/– MCH1 agonist, as described above in cAMP methods. Intracellular cAMP is extracted for analysis by radioimmunoassay. Other assays may be substituted for cAMP inhibition, including GTP$\gamma^{35}$S binding assays and inositol phosphate hydrolysis assays. Host cells transfected with MCH1 minus G alpha or with G alpha minus MCH1 would be tested simultaneously as negative controls. MCH1 receptor expression in transfected cells may be confirmed in radioligand binding studies using membranes from transfected cells. G alpha expression in transfected cells may be confirmed by Western blot analysis of membranes from transfected cells, using antibodies specific for the G protein of interest.

The efficiency of the transient transfection procedure is a critical factor for signal to noise in an inhibitory assay, much more so than in a stimulatory assay. If a positive signal present in all cells (such as forskolin-stimulated cAMP accumulation) is inhibited only in the fraction of cells successfully transfected with receptor and G alpha, the signal to noise ratio will be poor. One method for improving the signal to noise ratio is to create a stably transfected cell line in which 100% of the cells express both the receptor and the G alpha subunit. Another method involves transient co-transfection with a third cDNA for a G protein-coupled receptor which positively regulates the signal which is to be inhibited. If the co-transfected cells simultaneously express the stimulatory receptor, the inhibitory receptor, and a requisite G protein for the inhibitory receptor, then a positive signal may be elevated selectively in transfected cells using a receptor-specific agonist. An example involves co-transfection of COS-7 cells with 5-HT4 receptor, MCH1 receptor, and a G alpha sub-unit. Transfected cells are stimulated with a 5-HT4 agonist +/– MCH1 agonist. Cyclic AMP is expected to be elevated only in the cells also expressing MCH1 and the G alpha subunit of interest, and a MCH1-dependent inhibition may be measured with an improved signal to noise ratio.

It is to be understood that the cell lines described herein are merely illustrative of the methods used to evaluate the binding and function of the mammalian receptors of the present invention, and that other suitable cells may be used in the assays described herein.

Promiscuous Second Messenger Assays

It is possible to coax receptors of different functional classes to signal through a pre-selected pathway through the use of promiscuous $G_\alpha$ subunits. For example, by providing a cell based receptor assay system with an exogenously supplied promiscuous $G_o$ subunit such as $G_{\alpha 16}$ or a chimeric $G_\alpha$ subunit such as $G_{\alpha z q}$, a GPCR which normally might prefer to couple through a specific signaling pathway (e.g. $G_s$, $G_i$, $G_q$, $G_o$, etc.), can be made to couple through the pathway defined by the promiscuous $G_\alpha$ subunit and upon agonist activation produce the second messenger associated with that subunit's pathway. In the case of $G_{\alpha 16}$ and/or $G_{\alpha q z}$ this would involve activation of the $G_q$ pathway and production of the second messenger inositol phosphate. Through similar strategies and tools, it is possible to bias receptor signaling through pathways producing other second messengers such as $Ca^{+\leftrightarrows}$, cAMP, $K^+$ currents, etc.

Microphysiometric Assay

Because cellular metabolism is intricately involved in and effected by a broad range of cellular events (including receptor activation of various second messenger pathways), the use of microphysiometric measurements of cell metabolism can in principle provide a generic assay of cellular activity arising from the activation of any receptor regardless of the specifics of the receptor's proximal signaling pathway.

General guidelines for cell preparation and microphysiometric recording have been previously reported (Salon, J. A. and Owicki, J. A., 1996). A typical protocol employing transiently transfected CHO cells is as follows; 24 hours prior to recording, transfected cells are harvested and counted. $3 \times 10^5$ cells are seeded into cell culture capsules (Costar), and allowed to attach to the capsule membrane. 10 hours later (14 hours prior to recording) the cell media is switched to serum free F-12 complete to minimize ill-defined metabolic stimulation caused by assorted serum factors.

On the day of the experiment the cell capsules are transferred to the microphysiometer (Cytosensor, Molecular Devices Corporation, Sunnyvale, Calif.) and allowed to equilibrate in recording media (low buffered RPMI 1640, no bicarbonate, no serum) with 0.1% BSA (essentially fatty acid free), during which a baseline measurement of basal metabolic activity is established. The recording paradigm consists of a 100 µl/min flow rate, with a 2 min pump cycle which includes a 30 sec flow interruption during which the rate measurement is taken. Challenges involve a 1 min 20 sec exposure to a drug just prior to the first post challenge rate measurement being taken, followed by two additional pump cycles for a total of 5 min 20 sec drug exposure. Drug is then washed out and rates allowed to return to basal. Reported extracellular acidification rates are expressed as a percentage increase of the peak response over the baseline rate observed just prior to challenge.

GPCR Ligand Library

Functional assays of new receptors such as MCH1 may include a preliminary test of a small library of compounds containing representative agonists for all known GPCRs as well as other compounds which may be agonists for prospective GPCRS or which may be effectors for targets peripherally involved with GPCRs. The collection used in this study comprises approximately 180 compounds (including small molecules, hormones, preprohormones, peptides, etc.) for more than 45 described classes of GPCRs (serotonin, dopamine, noradrenaline, opioids, etc.) and additionally includes ligands for known or suspected but not necessarily pharmacological characterized or cloned GPCR families (such as MCH).

The diversity of the library can be expanded to include agonist and antagonist compounds specific for GPCR subtypes, combinatorial peptide and/or small molecule libraries, natural product collections, and the like. To facilitate robotic handling, the substances are distributed as either separate or pooled compound concentrates in 96 well plates and stored frozen as ready to use reagent plates.

Localization of mRNA codina for human MCH1 receptors Development of probes for MCH1: To facilitate the production of radiolabeled, antisense RNA probes a fragment of the gene encoding rat MCH1 will be subcloned into a plasmid vector containing RNA polymerase promoter sites. The full length cDNA encoding the rat MCH1 will be digested with Pst 1, (nucleotides 905–1194) and this 289 nucleotide fragment will be cloned into the Pst I site of PGEM 3z, containing both sp6 and T7 RNA polymerase promoter sites. The construct will be sequenced to confirm sequence identity and orientation. To synthesize antisense strands of RNA, this construct will be linearized with Hind III or Eco RI (depending on orientation) and T7 or sp6 RNA polymerase will be used to incorporate radiolabeled nucleotide as described below.

A probe coding for the rat glyceraldehyde 3-phosphate dehydrogenase (GAPDH) gene, a constitutively expressed protein, was used concurrently. GAPDH is expressed at a relatively constant level in most tissue and its detection is used to compare expression levels of the rat MCH1 receptors gene in different regions.

Synthesis of probes: MCH1 and GAPDH cDNA sequences preceded by phage polymerase promoter sequences will be used to synthesize radiolabeled riboprobes. Conditions for the synthesis of riboprobes will be: 0.25–1.0 µg linearized DNA plasmid template, 1.5 µl of ATP, GTP, UTP (10 mM each), 3 µl dithiothreitol (0.1 M), 30 units RNAsin RNAse inhibitor, 0.5–1.0 µl (15–20 units/µl) RNA polymerase, 7.0 µl transcription buffer (Promega Corp.), and 12.5 µl $\alpha^{32}$P-CTP (specific activity 3,000 Ci/mmol). 0.1 mM CTP (0.02–1.0 µl) will be added to the reactions, and the volume will be adjusted to 35 µl with DEPC-treated water. Labeling reactions will be incubated at 37° C. for 60 min, after which 3 units of RQ1 RNAse-free DNAse (Promega Corp.) will be added to digest the template. Riboprobes will be separated from unincorporated nucleotides using Microspin S-300 columns (Pharmacia Biotech). TCA precipitation and liquid scintillation spectrometry will be used to measure the amount of label incorporated into the probe. A fraction of all riboprobes synthesized will be size-fractionated on 0.25 mm thick 7M urea, 4.5% acrylamide sequencing gels. These gels will be apposed to storage phosphor screens and the resulting autoradiograph scanned using a phoshorimager (Molecular Dynamics, Sunnyvale, Calif.) to confirm that the probes synthesized were full-length and not degraded.

Solution hybridization/ribonuclease protection assay (RPA): For solution hybridization 2.0 µg of mRNA isolated from tissues will be used. Negative controls consisted of 30 µg transfer RNA (tRNA) or no tissue blanks. All mRNA samples will be placed in 1.5-ml microfuge tubes and vacuum dried. Hybridization buffer (40 µl of 400 mM NaCl, 20 mM Tris, pH 6.4, 2 mM EDTA, in 80% formamide) containing 0.25–2.0 $E^6$ counts of each probe will be added to each tube. Samples will be heated at 95° C. for 15 min, after which the temperature will be lowered to 55° C. for hybridization.

After hybridization for 14–18 hr, the RNA/probe mixtures will be digested with RNAse A (Sigma) and RNAse T1 (Life Technologies). A mixture of 2.0 µg RNAse A and 1000 units of RNAse T1 in a buffer containing 330 mM NaCl, 10 mM Tris (pH 8.0) and 5 mM EDTA (400 µl) will be added to each sample and incubated for 90 min at room temperature. After digestion with RNAses, 20 µl of 10% SDS and 50 µg proteinase K will be added to each tube and incubated at 37° C. for 15 min. Samples will be extracted with phenol/chloroform:isoamyl alcohol and precipitated in 2 volumes of ethanol for 1 hr at −70° C. Pellet Paint (Novagen) will be added to each tube (2.0 µg) as a carrier to facilitate precipitation. Following precipitation, samples will be centrifuged, washed with cold 70% ethanol, and vacuum dried. Samples will be dissolved in formamide loading buffer and size-fractionated on a urea/acrylamide sequencing gel (7.0 M urea, 4.5% acrylamide in Tris-borate-EDTA). Gels will be dried and apposed to storage phosphor screens and scanned using a phosphorimager (Molecular Dynamics, Sunnyvale, Calif.).

RT-PCR: For the detection of RNA encoding human MCH1, RT-PCR was carried out on mRNA extracted from human tissue. Reverse transcription and PCR reactions were carried out in 50 ml volumes using EZrTth DNA polymerase (Perkin Elmer). Primers with the following sequences were used:

Forward primer (RA SLCla/MCH F); TCA GCT CGG TTG TGG GAG CA (Seq. I.D. No. 14)

Reverse primer (RA/SLCia MCH B); CTT GGA CTT CTT CAC GAC (Seq. I.D. No. 15)

These primers will amplify a 248 base pair fragment from nucleotide 169 to 417.

Each reaction contained 0.1 µg mRNA and 0.3 µM of each primer. Concentrations of reagents in each reaction were: 300 µM each of GTP; DATP; dCTP; dTTP; 2.5 mM Mn(OAc)2; 50 mM Bicine; 115 mM potassium acetate, 8% glycerol and 5 units EZrTth DNA polymerase. All reagents for PCR (except mRNA and oligonucleotide primers) were obtained from Perkin Elmer. Reactions were carried out under the following conditions: 65° C. 60 min., 94° C. 2 min., (94° C., 1 min., 65° C. 1 min) 35 cycles, 72° C. 10 min.

PCR reactions were size fractionated by gel electrophoresis using $10^6$ polyacrylamide. DNA was stained with SYBR Green I (Molecular Probes, Eugene Oreg.) and scanned on a Molecular Dynamics (Sunnyvale Calif.) Storm 860 in blue fluorescence mode at 450 nM.

Positive controls for PCR reactions consisted of amplification of the target sequence from a plasmid construct, as well as reverse transcribing and amplifying a known sequence. Negative controls consisted of mRNA blanks, as well as primer and mRNA blanks. To confirm that the mRNA was not contaminated with genomic DNA, samples were digested with RNAses before reverse transcription. Integrity of RNA was assessed by amplification of mRNA coding for GAPDH.

Results and Discussion Cloning and Sequencing

Discovery of an Expressed Sequence Tag (EST) F07228 in GENEML Homologous to FB41a A BLAST search of GENEMBL with a Synaptic Pharmaceutical Corporation proprietary sequence, FB41a, resulted in the identification of an EST (accession number F07228) with a high degree of homology to FB41a and somatostatin, opiate and galanin receptors.

Construction and Screening of a Human Hippocampal cDNA Library

A human hippocampal cDNA library containing a total of $2.2 \times 10^6$ independent clones with a mean insert size of 3.0 kb was prepared in the expression vector PEXJ.BS. The library was plated on agar plates (ampicillin selection) and glycerol stocks for 450 pools of 5000 independent clones were prepared. Primary glycerol stocks were also grouped together in groups of approximately 10 to create superpools.

Cloning of the Full-Length Sequence of MCH1

Glycerol stocks of the superpools and primary pools from the human hippocampal cDNA library were screened by PCR with F07228 specific primers T579 and T580. One positive primary pool 490, was successively divided into subpools, amplified in LB medium overnight and screened by PCR using primers T579 and T580. One positive subpool, 490-4-10-23 was plated on agar plates (ampicillin selection), and colonies were transferred to nitrocellulose membranes (Schleicher and Schuell, Keene, N.H.). Filters were hybridized for two days under high stringency conditions with $10^6$ cpm/ml of a $^{32}$P-labeled cDNA probe, T581, designed against the F07228 EST sequence. Filters were washed and apposed to Biomax MS film (Kodak). Seven positive colonies were picked, streaked on LB-AMP plates, and grown overnight. Two individual colonies from each of the original seven were picked and subjected to vector-anchored PCR using the following primer pairs: T95, T580 and T94, T579. One positive colony, G1, was amplified overnight in TB and processed for plasmid purification. This plasmid was designated TL230 and sequenced on both strands. Nucleotide and peptide sequence analysis were performed with GCG programs (Genetics Computer Group, Madison, Wis.). A HindIII—KpnI fragment of TL230 was subcloned into the mammalian expression vector pEXJ, and named TL231. The largest open reading frame in this construct contains 1266 nucleotides (FIG. 1), which is predicted to encode a protein of 422 amino acids (FIG. 2). There are three in-frame methionines in the amino terminus which could result in a protein of 422, 417 or 353 amino acids. Hydropathy analysis of the protein is consistent with a putative topography of seven transmembrane domains, indicative of the G protein-coupled receptor family (FIG. 3). TL231 has been named MCH1.

Database analysis of the sequence of MCH1 revealed that it was most similar to somatostatin receptors. Further database analysis revealed a Genbank submission (accession number AF008650, deposited on Oct. 1, 1997) which appears to be the rat homologue of TL231. AF008650 is 69 nucleotides shorter than MCH1 at the 5'end, and predicts a different initiating methionine. FIGS. 4 and 5 illustrate the nucleotide and amino acid sequence for the rat MCH1 receptor, respectively.

Inositol Phosphate Response of MCH1-Transfected Cells

The expression vector (pEXJ) containing the MCH1 cDNA was transfected by electroporation into Cos-7 cells in combination with an expression vector (pEXJ) containing the $G_{\alpha 16}$ subunit. After plating and labeling with [$^3$H]-myo-inositol, the transfectants were challenged with a ligand library that included, among other things, melanin concentrating hormone (MCH) (10 μM final concentration) and then assayed for inositol phosphate (IP) formation. In five out of the seven screens, cells transfected with MCH1 (with $G_{\alpha 16}$) gave an approximately 1.4-fold increase in IP production as compared to cells transfected with $G_{\alpha 16}$ alone when challenged with MCH.

Subsequent experiments demonstrated that 10 μM MCH was able to stimulate IP release 3.4-fold over basal levels in Cos-7 cells transfected with MCH1 alone, suggesting that this receptor couples through the $G_q$ signaling pathway. The IP response was shown to be dose-dependent to MCH with an $EC_{50}$ value of 9.3±1.7 nM (n=2) and an $E_{max}$ of approximately 400% basal (404±72) (FIG. 6).

Figure 7:
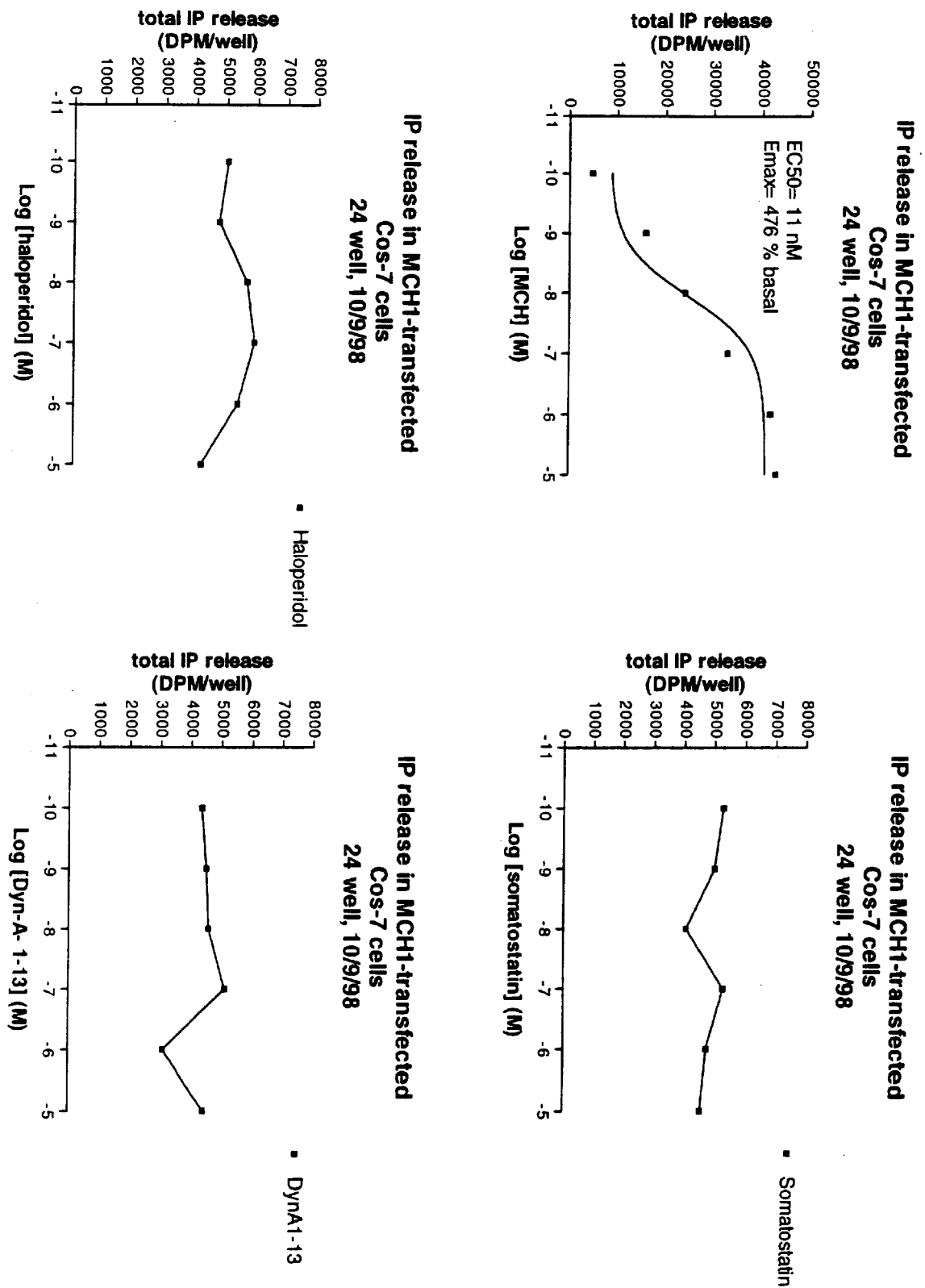
FIG. 7 MCH1 challenge with several compounds of interest.

Several additional compounds were tested for their ability to activate MCH1. No dose-responsiveness of inositol phosphate formation could be detected in Cos-7 cells transfected with MCH1 when challenged with somatostatin, haloperidol, or dynorphin A1-13, discounting the possibility that MCH1 encodes a somatostatin-like or opioid-like or sigma-like GPCR subtype (FIG. 7)

Microphysiometric Response of MCH1-Transfected Cells to MCH

Figure 8:
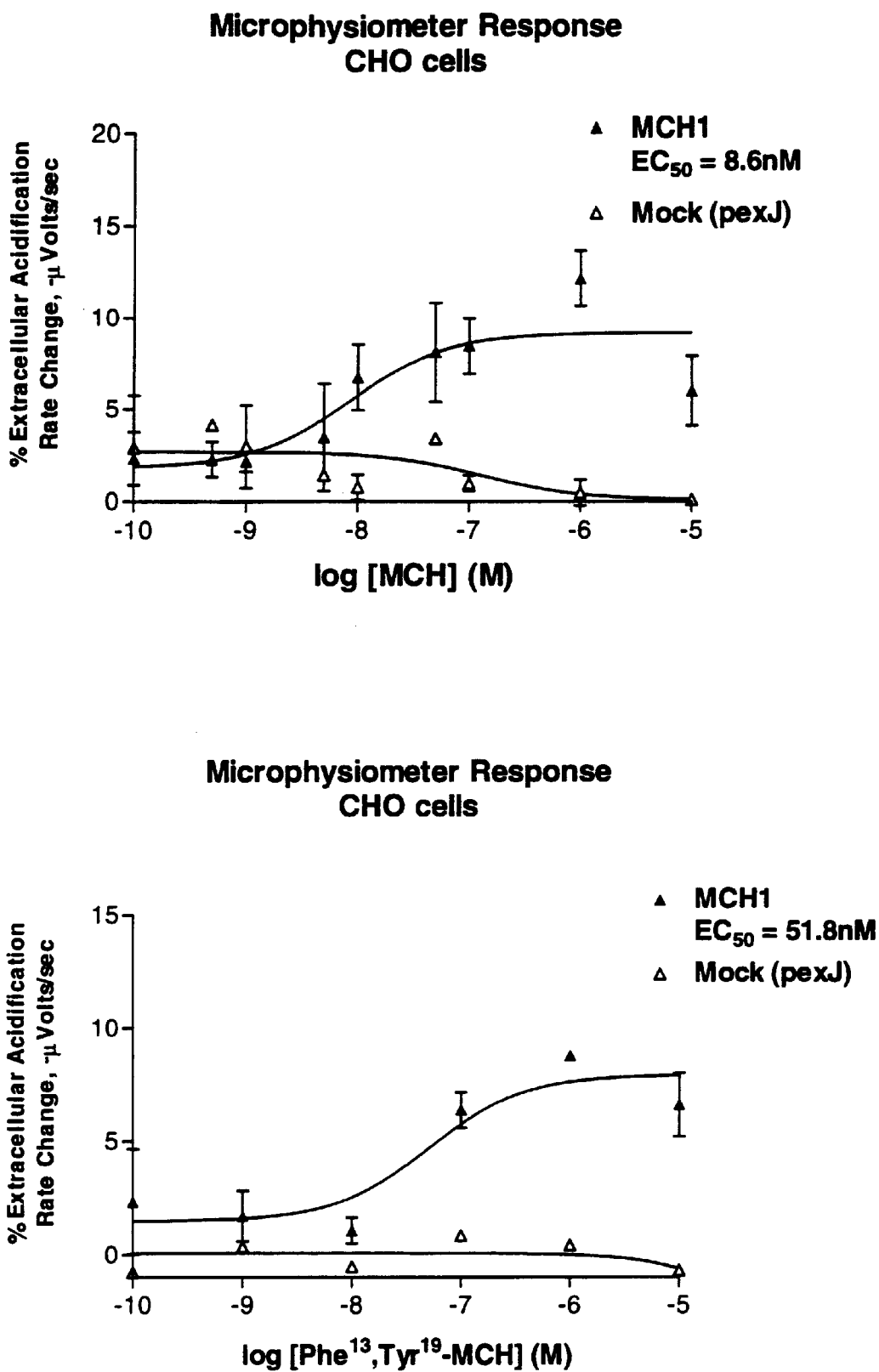
FIG. 8 MCH1-mediated extracellular acidification response to MCH and Phe$^{13}$,Tyr$^{19}$-MCH. Results are reported as the average of two independent experiments performed in duplicate.

CHO cells were transiently transfected with MCH1 using lipofectant, challenged with increasing concentrations of MCH or Phe$^{13}$,Tyr$^{19}$-MCH, and subsequently monitored for changes in extracellular acidification rates. Both ligands produced a dose-dependent increase in acidification rate with an $EC_{50}$ value of 8.6 nM for MCH and 51.8 nM for Phe$^{13}$,Tyr$^{19}$-MCH. Neither native CHO cells or mock (pEXJ) transfected CHO cells exhibited a change in acidification rate when exposed to MCH or Phe$^{13}$,Tyr$^{19}$-MCH (FIG. 8).

Transcriptional Response of MCH1-Transfected Cells

Figure 9:
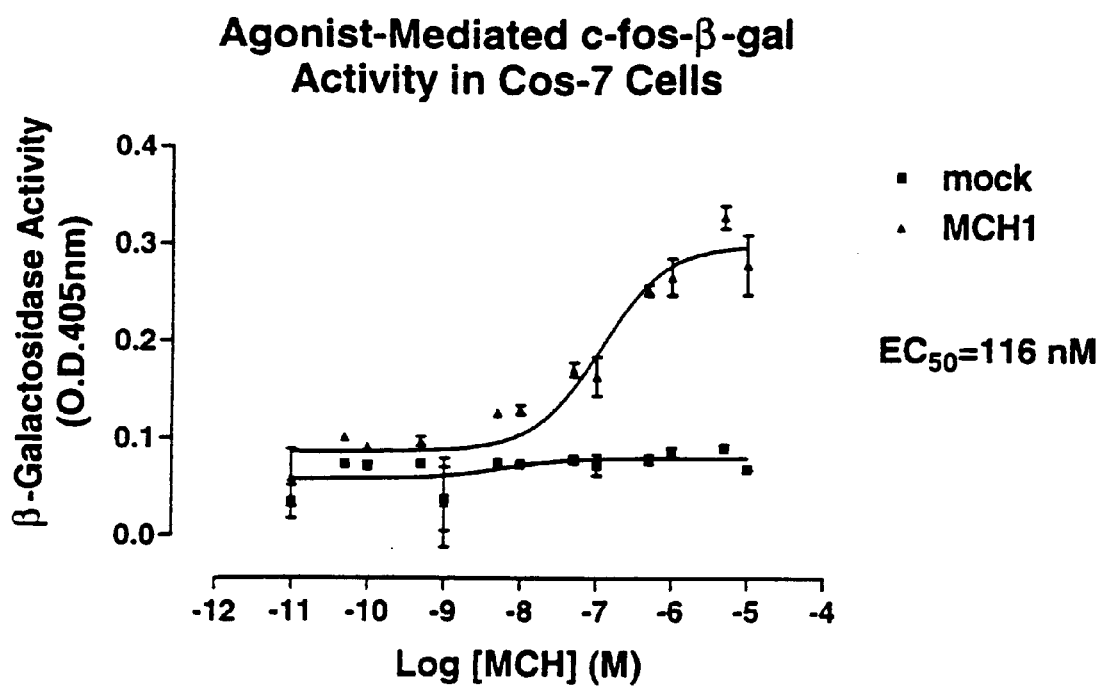
FIG. 9 Transcriptional response of MCH1-transfected Cos-7 cells to MCH.

Cos-7 cells were transiently transfected with MCH1 and a c-fos-β-gal reporter construct by the DEAE-dextran method. The cells were challenged with assorted drugs, including MCH, and transcriptional activity measured by colorimetric assay of β-galactosidase protein expression. Initial single dose challenges with MCH at a concentration of 10 μM stimulated c-fos-regulated transcriptional activity approximately 3.9-fold over cells challenged with medium only. Cells transfected with only the c-fos-β-gal construct showed no response to MCH. Subsequent experimentation showed the transcription activation response to be dose-dependent to MCH with an $EC_{50}$ value of 116 nM (FIG. 9).

Binding of [$^{125}$I]Phe$^{13}$,Tyr$^{19}$-MCH in MCH1-Transfected Cells

Membranes harvested from Cos-7 cells transfected with MCH1 by the DEAE-dextran method exhibited specific binding for [$^{125}$I]Phe$^{13}$-Tyr$^{19}$-MCH (about 80 fmol/mg membrane protein) over mock-transfected cells (about 20 fmol/mg membrane protein) at 0.1 nM radioligand concentration. Specific [$^{125}$I]Phe$^{13}$-Tyr$^{19}$-MCH binding was about 70% of total binding at a radioligand concentration of 0.1 nM (FIG. 10).

Localization of mRNA Encoding Human MCH1 Receptors

Figure 11:
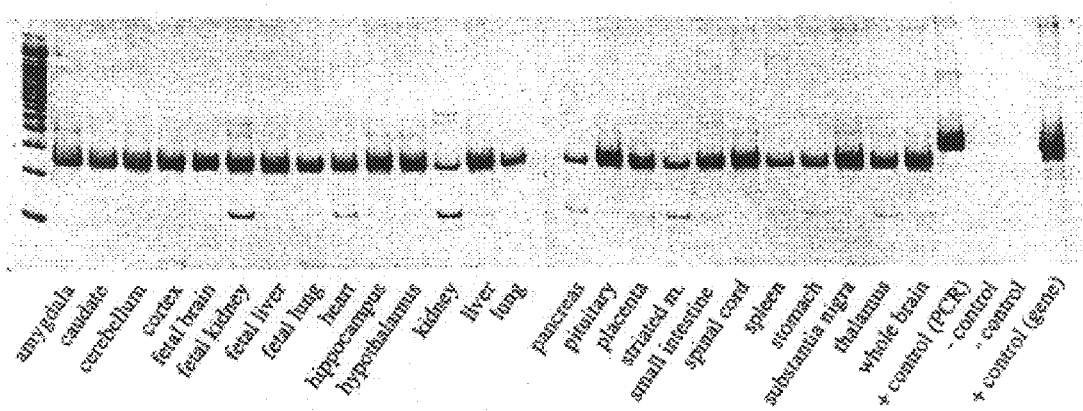
FIG. 11 RT-PCR detection of MCH1 receptor mRNA in human mRNA samples.

RT-PCR was used to assess the presence of MCH1 receptor encoding message in mRNA samples isolated from a variety of human tissues (Table 1, FIG. 11). After amplification, PCR reactions were size fractionated on 10% polyacrylamide gels, and stained with SYBR Green I. Images were analyzed using a Molecular Dynamics Storm 860 workstation. The amplified band corresponding to MCH1 receptor (490 base pairs) is indicated (arrow) RT-PCR analysis indicates the distribution of MRNA encoding human MCH1 receptor is widespread throughout all tissues assayed, including both central nervous system tissue and peripheral organs. This widespread distribution implies broad regulatory functions that involve nervous system as well as endocrine mechanisms.

TABLE 1

Distribution of mRNA coding for human MCH1 receptors.

| Region | human MCH 1 | Potential applications |
| --- | --- | --- |
| liver | +++ | Diabetes |
| kidney | +++ | Hypertension, Electrolyte balance |
| lung | +++ | Respiratory disorders, asthma |
| heart | +++ | Cardiovascular indications |
| small intestine | +++ | Gastrointestinal disorders |
| striated muscle | +++ | Musculoskeletal disorders |
| pituitary | +++ | Endocrine/neuroendocrine regulation |
| whole brain | +++ | |
| amygdala | +++ | Depression, phobias, anxiety, mood disorders |
| cerebral cortex | +++ | Sensory and motor integration, cognition |
| hippocampus | +++ | Cognition/memory |
| hypothalamus | +++ | appetite/obesity, neuroendocrine regulation |
| spinal cord | +++ | Analgesia, sensory modulation and transmission |
| cerebellum | +++ | Motor coordination |
| thalamus | +++ | sensory integration |
| substantia nigra | +++ | Modulation of dopaminergic function. Modulation of motor coordination. |
| caudate-putamen | +++ | Modulation of dopaminergic function |
| fetal brain | +++ | Developmental disorders |
| fetal lung | +++ | Developmental disorders |
| fetal kidney | +++ | Developmental disorders |
| fetal liver | +++ | Developmental disorders |

The cloning of the gene encoding the human MCH1 receptor has provided the means to explore its physiological role by pharmacological characterization, and by Northern and in situ mapping of its mRNA distribution. Further, the availability of the DNA encoding the human MCH1 receptor will facilitate the development of antibodies and antisense technologies useful in defining the functions of the gene products in vivo. Antisense oligonucleotides which target mRNA molecules to selectively block translation of the gene products in vivo have been used successfully to relate the expression of a single gene with its functional sequelae. Thus, the cloning of this receptor gene provides the means to explore its physiological role in the nervous system and elsewhere, and may thereby help to elucidate structure/function relationships within the GPCR superfamily.

REFERENCES

Abrao, M. S., Castrucci, A. M., Hadley, M. E. and Hruby, V. J. (1991) Protein-kinase-C mediates MCH signal transduction in teleost, *Synbranchus marmoratus*, melanocytes. Pigment. Cell. Res. 4:66–67.

Auburger, G., Gispert, S., Scheufler, K., Nothers, C., Lunkes, A., Hernandez, A., Magarino, C., Enczmann, J., Freund, H. J., Heredero, L., and Orozco, G. (1992) Assignment of the second (cuban) locus of autosomal dominant cerebellar ataxia to chromosome 12q23–24.1, between flanking markers D12S58 and PLA2. Cytogenet. Cell. Genet. 61:252–256.

Bahjaoui-Bouhaddi, M., Fellmann, D., Griffond, B. and Bugnon, C. (1994) Insulin treatment stimulates the rat melanin-concentrating hormone-producing neurons. Neuropeptides 24:251–258.

Baker, B. I. (1991) Melanin-concentrating hormone: a general vertebrate neuropeptide. Int. Rev. Cytol. 126:1–47.

Baker, B. I. (1994) Melanin-concentrating hormone update: functional consideration. TEM 5:120–126.

Bassett, A. S., Jones, B. D., McGillivray, B. C. and Pantzer, J. T. (1988) Partial trisomy chromosome 5 cosegregating with schizophrenia. Lancet 1:799–801.

Bittencourt, J. C., Presse, F., Arias, C., Peto, C., Vaughan, J., Nahon, J. L., Vale, W., Sawchenko, P. E. (1992) The melanin-concentrating hormone system of the rat brain: An immuno- and hybridization histochemical characterization . J. Comp. Neurol. 319:218–245.

Bradford, M. M. (1976) A rapid and sensitive method for the quantitation of microgram quantities of protein utilizing the principle of protein-dye binding. Anal Biochem May 7, 1976; 72:248–54.

Breton, C., Schorpp, M., and Nahon, J. L. (1993) Isolation and characterization of the human melanin-concentrating hormone gene and a variant gene. Mol. Brain Res. 18:297–310.

Burgaud, J. L., Poosti, R., Fehrentz, J. A., Martinez, J., and Nahon, J. L. (1997) Melanin-concentrating hormone binding sites in human SVK14 keratinocytes. Biochem. Biophys.Res.Commun. 241 (3):622–629.

Burns, C. C., Moser, M., Banks, J., Alderete, J. P., and Overbaugh, J. (1996) Identification and deletion of sequences required for feline leukemia virus RNA packaging and construction of a high-titer feline leukemia virus packaging cell line. Virology (Aug. 1, 1996) 222 (1):14–20.

Chu, Y. Y., Tu, K. H., Lee, Y. C., Kuo, Z. J., Lai, H. L., and Chern, Y. (1996) Characterization of the rat A2a adenosine receptor gene. DNA Cell Biol (April 1996) 15 (4):329–37.

Coleman, A. (1984) Transcription and Translation: A Practical Approach (B. D. Hanes, S. J. Higgins, eds., pp 271—302, IRL Press, Oxford, 1984).

Craddock, N., Dawson, E., Burge, S., Parfitt, L., Mant, B., Roberts, Q., Daniels, J., Gill, M., McGuffin, P., Powell, J. and Owen, M. (1993) The gene for Darier's disease maps to chromosome 12q23–q24.1. Hum. Mol. Genet. 2:1941–1943.

Dascal, N., Schreibmayer, W., Lim, N. F., Wang, W., Chavkin, C., DiMagno, L., Labarca, C., Kieffer, B. L., Gaveriaux-Ruff, C., Trollinger, D., Lester, H. A., Davidson, N. (1993) Atrial G protein-activated K+ channel.: expression cloning and molecular properties. Proc. Natl. Acad. Sci. U.S.A. 90:10235–10239.

Drozdz, R. and Eberle, A. N. (1995) Binding sites for melanin-concentrating hormone (MCH) in brain synaptosomes and membranes from peripheral tissues identified with highly tritiated MCH. J.Recept.Signal.Transduct.Res. 15(1–4):487–502.

Drozdz, R., Siegrist, W., Baker, B. I., Chluba-de Tapia, J. and Eberle, A. N. (1995) Melanin-concentrating hormone binding to mouse melanoma cells in vitro. FEBS 359:199–202.

Drozdz, R., Hintermann, E., and Eberle A. N. (1998) Characterization of the receptor for melanin-concentrating hormone on melanoma cells by photocrosslinking. Ann.NY Acad.Sci. 839(1):210–213.

Fong, T. M.; Huang, R. C.; Yu, H.; Swain, C. J.; Underwood, D.; Cascieri, M. A.; Strader, C. D. (1995) Mutational analysis of neurokinin receptor function. Can. J. Physiol. Pharmacol. 73(7):860–865 (July 1995).

Gilliam, T. C., Freimer, N. B., Kaufmann, C. A., Powchik, P. P., Bassett, A. S., Bengtsson, U. and Wasmuth, J. J. (1989) Deletion mapping of DNA markers to a region of chromosome 5 that cosegregates with schizophrenia. Genomics 5:940–944.

Gonzalez, M. I., Baker, B. I., and Wilson, C. A. (1997) Stimulatory effect of melanin-concentrating hormone on luteinizing hormone release. Neuroendocrinology. 66 (4):254–262.

Gonzalez, M. I., Kalia, V., Hole, D. R. and Wilson, C. A. (1997) α-melanocyte-stimulating hormone (α-MSH) and melanin-concentrating hormone (MCH) modify monoaminergic levels in the preoptic area of the rat. Peptides 18:387–392.

Gonzalez, M. I., Vazira, S., and Wilson, C. A. (1996) Behavioral effects of α-melanocyte-stimulating hormone (α-MSH) and melanin-concentrating hormone (MCH) after central administration in female rats. Peptides 17:171–177.

Graziano, M. P.; Hey, P. J.; Strader, C. D. (1996)The amino terminal domain of the glucagon-like peptide-1 receptor is a critical determinant of subtype specificity. Receptors Channels 4(1):9–17.

Grillon, S., Herve, C., Griffond, B., and Fellmann, D. (1997) Exploring the expression of the melanin-concentrating hormone messenger RNA in the rat lateral hypothalamus after goldthioglucose injection. Neuropeptides 31(2) :131–136.

Guan, X. M.; Amend, A.; Strader, C. D. (1995) Determination of structural domains for G protein coupling and ligand binding in beta 3-adrenergic receptor. Mol. Pharmacol. 48(3):492–498 (September 1995).

Gundersen, C. B., Miledi, R., and Parker, I. (1983) Serotonin receptors induced by exogenous messenger RNA in Xenopus oocytes. Proc R Soc Lond B Biol Sci (Aug. 22, 1983) 219:1214 103–9.

Herve, C. and Fellmann, D. (1997) Changes in rat melanin-concentrating hormone and dynorphin messenger ribonucleic acids induced by food deprivation. Neuropeptides 31(3):237–242.

Hervieu, G. and Nahon, J. L. (1995) Pro-melanin concentrating hormone messenger ribonucleic acid and peptides expression in peripheral tissues of the rat. Neuroendocrinology. 61(4):348–364.

Hervieu, G., Segretain, D. and Nahon, J-L. (1996) Development and stage-dependent expression of melanin-concentrating hormone in mammalian germ cells. Biology of Reproduction 54:1161–1172.

Kauwachi, H., Kawazoe, I., Tsubokawa, M., Kishida, M. and Baker, B. I. (1983) Characterization of melanin-concentrating hormone in chum salmon pituitaries. Nature 305:321–333.

Knigge, K. M., Baxter-Grillo, D., Speciale, J. and Wagner, J. (1996) Melanotropic peptides in the mammalian brain: The melanin-concentrating hormone. Peptides 17:1063–1073.

Knigge, K. M. and Wagner, J. E. (1997) Melanin-concentrating hormone (MCH) involvement in pentylenetetrazole (PTZ)-induced seizure in rat and guinea pig. Peptides 18(7):1095–1097.

Krapivinsky, G., Gordon, E. A., Wickman B., Velimirovic, B., Krapivinsky, L., Clapham, D. E. (1995) The G-protein-gated atrial K+ *channel IKACh is a heteromultimer of two inwardly rectifying K(+)-channel proteins.* Nature 374:135–141.

Krapivinsky, G., Krapivinsky, L., Velimirovic, B., Wickman, K., Navarro, B., Clapham, D. E., (1995b) The cardiac inward rectifier K+ channel subunit, CIR, does not comprise the ATP-sensitive K+ channel, IKATP. J. Biol. Chem. 270: 28777–28779.

Kubo, Y., Reuveny, E., Slesinger, P. A., Jan, Y. N., Jan, L. Y. (1993) Primary structure and functional expression of a rat G-protein-coupled muscarinic potassium channel. Nature 364: 802–806.

Lazareno, S. and Birdsall N. J. M. (1993) Pharmacological characterization of acetylcholine stimulated [$^{35}$S]-GTPγS binding mediated by human muscarinic m1–m4 receptors: antagonist studies. Br. J. Pharmacology, 109: 1120–1127.

Ludwig, D. S., Mountjoy, K. G., Tatro, J. B., Gillette, J. A., Frederich, R. C., Flier, J. S., and Maratos-Flier, E. (1998) Melanin-concentrating hormone: a functional melanocortin antagonist in the hypothalamus. Am.J.Physiol.Endocrinol.Metab. 274(4):E627–E633.

MacKenzie, F. J., Hunter, A. J., Daly, C., Wilson, C. A. (1984) Evidence that the dopaminergic incerto-hypothalamic tract has a stimulatory effect on ovulation and gonadotropin release. Neuroendocrinology 39:289–295.

Masu, Y. et al. (1994) Nature 329:21583–21586.

McBride, R. B., Beckwith, B. E., Swenson, R. R., Sawyer, T. K., Hadley, M. E., Matsunaga, T. O. and Hruby, V. J. (1994) The actions of melanin-concentrating hormone (MCH) on passive avoidance in rats: A preliminary study. Peptides 15:757–759.

Melki, J., Abdelhak, S., Sheth, P., Bachelot, M. F., Burlet, P., Marcadet, A., Aicardi, J., Barois, A., Carriere, J. P., Fardeau, M., Fontan, D., Ponsot, G., Billette, T., Angelini, C., Barbosa, C., Ferriere, G., Lanzi, G., Ottolini, A., Babron, M. C., Cohen, D., Hanauer, A., Clerget-Darpoux, G., Lathrop, M., Munnich, A. and Frezal, J. (1990) Gene for chronic proximal spinal muscular atrophies maps to chromosome 5q. Nature (London) 344:767–768.

Miller, C. L., Hruby, V., Matsubaga, T., Bickford, P. (1993) α-MSH and MCH are functional antagonists in a CNS auditory paradigm. Peptides 14:1–10.

Miller, J., Germain, R. N., Efficient cell surface expression of class II MHC molecules in the absence of associated invariant chain. J.Exp.Med. 164:1478–1489 (1986).

Morishita, F., Hashito, K., Fujimoto, M. and Yamada, K. (1993) Possible involvement of pertussis toxinsensitive GTP-binding protein in the α2-adrenoceptormediated melanosome-aggregation response of goldfish melanophores. J. Exp. Zoology 266:173–180.

Nahon, J. L., Presse, F., Bittencourt, J. C., Sawchenko, P., and Vale, W. (1989) The rat melanin-concentrating hormone mRNA encodes multiple putative neuropeptides coexpressed in the dorsolateral hypothalamus. Endocrinology 125:2056–2065.

Nahon, J-L. (1994) The melanin-concentrating hormone: from the peptide to the gene. Critical Rev. in Neurobiol 221:221–262.

Parkes, D. G. (1996) Diuretic and natriuretic actions of melanin concentrating hormone in conscious sheep. J. Neuroendocrinol. 8:57–63.

Parkes, D. and Vale, W. (1993) Secretion of melanin-concentrating hormone and neuropeptide-EI from cultured rat hypothalamic cells. Endocrinology 131:1826–1831.

Pedeutour, F., Szpirer, C. and Nahon, J. L. (1994) Assignment of the human pro-melanin-concentrating hormone gene (PMCH) to chromosome 12q23–24 and two variant genes (PMCHL1 and PMCHL2) to chromosome 5p14 and 5q12–q13. Genomics 19:31–37.

Presse, F., Hervieu, G., Imaki, T., Sawchenko, P. E., Vale, W., and Nahon, J-L. (1992) Rat melanin-concentrating hormone messenger ribonucleic acid expression: marked changes during development and after stress and glucocorticoid stimuli. Endocrinology 131:1241–1250.

Qu, D., Ludwig, D. S., Gammeltoft, S., Piper, M., Pelleymounter, M. A., Cullen, M. J., Foulds Mathes, W., Przypek, J., Kanarek, R. and Maratos-Flier, E. (1996) A role for melanin-concentrating hormone in the central regulation of feeding behaviour. Nature 380:243–247.

Qu, D., Mastaitis, J. W., Tritos, N. A. and Maratos-Flier, E. (1998) 80$^{th}$ Annual Meeting of the Endocrine Society in New Orleans. Abs. # P1-494.

Quick, M. W., Lester, H. A. Methods for expression of excitability proteins in Xenopus oocytes. Meth. Neurosci. 19:261–279 (1994).

Rossi, M., Choi, S. J., O'Shea, D., Miyoshi, T., Ghatei, A. and Bloom, S. R. (1997) Melanin-concentrating hormone acutely stimulates feeding, but chronic administration has no effect on body weight. Endocrinology 138:351–355.

Sahu, A. (1998) Evidence suggesting that galanin (GAL), melanin-concentrating hormone (MCH), neurotensin (NT), proopiomelanocortin (POMC) and neuropeptide Y (NPY) are targets of leptin signaling in the hypothalamus. Endocrinology 139(2):795–798.

Sakurai, T., Amemiya, A., Ishii, M., Matsuzaki, I., Chemelli, R. M. et al., (1998) Orexins and orexin receptors: A family of hypothalamic neuropeptides and G protein-coupled receptors that regulate feeding behavior. Cell 92:573–585.

Salon, J. A. and Owicki, J. C. (1995) Real-time measurements of receptor activity: Applications of microphysiometric techniques to receptor biology. In: Methods in Neuroscience 25:201–223 (Academic Press, 1995).

Sambrook, J., Fritsch, E. F., and Maniatis, T., In: Molecular Cloning: A Laboratory Manual, 2nd Edition (Cold Spring Harbor Laboratory, Cold Spring Harbor, N.Y.), 1989.

Sanchez, M., Baker, B. I. and Celis, M. (1997) Melanin-concentrating hormone (MCH) antagonizes the effects of α-MSH and neuropeptide E-I on grooming and locomotor activities in the rat. Peptides 18:393–396.

Schilling K., Luk, D., Morgan J., and Curran, T (1991) Regulation of a fos-lacZ fusion gene: A paradigm for quantitative analysis of stimulus transcription coupling. Proc. Nat. Acad. Sci (U.S.A.) 88:5665–5669.

Sherrington, R., Brynjolfsson, J., Petursson, H., Potter, M., Dudleston, K., Barraclough, B., Wasmuth, J., Dobbs, M. and Gurling, H. (1988) Localization of a susceptibility locus for schizophrenia on chromosome 5. Nature (London) 336:164–167.

Spurney, R. F.; Coffman, T. M. (1997) The C-terminus of the thromboxane receptor contributes to coupling and desensitization in a mouse mesangial cell line. J. Pharmacol. Exp. Ther. 283(1):207–215 (October 1997).

Stuart, R. O., Sun, A., Bush, K. T., and Nigam, S. K. (1996) Dependence of epithelial intercellular junction biogenesis on thapsigargin-sensitive intracellular calcium stores. J Biol Chem (Jun. 7, 1996) 271(23):13636–41.

Svenssson, S. P., Norberg, T., Andersson, R. G., Grundstrom, N. and Karlsson, J. O. G. (1991) MCH-induced pigment aggregation in teleost melanophores is associated with a cAMP reduction. Life Sci. 48:2043–2046.

Takahashi, T., Neher, E., and Sakmann, B. (1987) Rat brain serotonin receptors in Xenopus oocytes are coupled by intracellular calcium to endogenous channels. Proc Natl Acad Sci U.S.A. (1987 July) 84(14):5063–7.

Tian, W., Duzic, E., Lanier, S., and Deth R. (1994) Determinants of α-Adrenergic Receptor Activation of G protein: Evidence for a Precoupled Receptor/G protein State. Molecular Pharmacology, 45:524–531.

Toumaniantz, G., Bittencourt, J. C., and Nahon, J. L. (1996) The rat melanin-concentrating hormone gene encodes an additional putative protein in a different reading frame. Endocrinology 137:4518–4521.

Twells, R., Weber, J., Orozco, G., Farrell, M., Williamson, R. and Chamberlain, S. (1992) Chromosomal assignment of the locus causing olivo-ponto-cerebellar atrophy (SCA2) in a cuban founder population. Cytogent. Cell. Cenet. 61:262–265.

Underwood, D. J., Strader, C. D., Rivero, R., Patchett, A. A., Greenlee, W., and Prendergast, K. (1994) Structural model of antagonist and agonist binding to the angiotensin II, AT1 subtype, G protein coupled receptor. Chem Biol (1994 December ) 1(4):211–21.

Viale, A., Zhixing, Y., Breton, C., Pedeutour, F., Coquerel, A., Jordan, D., Nahon, J. L. (1997) The melanin-concentrating hormone gene in human: flankina region analysis, fine chromosome mapping, and tissue-specific expression. Mol. Brain Res. 46:243–255.

Westbrook, C. A., Neuman, W. L., McPherson, J., Camper, S., Wasmuth, J., Plaetke, R. and Williamson, R. (1992) Report of the second international workshop on human chromosome 5 mapping. Cytogenet. Cell. Genet. 61:225–231.

Yalkinoglu, A. O., Spreyer, P., Bechem, M., Apeler, N., and Wohlfeil, S. (1995) Induction of c-fos expression in rat vascular smooth muscle reporter cell by selective activation of the thrombin receptor. J. Receptor and Signal Transduction, 15(1–4):117–130.

What is claimed is:

1. A process for determining whether a chemical compound is a human Melanin-concentrating hormone 1 (MCH1) receptor antagonist which comprises contacting cells transfected with and expressing DNA encoding the human MCH1 receptor with the compound in the presence of a known human MCH1 receptor agonist, under conditions permitting the activation of the human MCH1 receptor, and detecting human MCH1 receptor activity, wherein a decrease in human MCH1 receptor activity in the presence of both the compound and the known agonist relative to the activity of the human MCH1 receptor in the presence of the known agonist alone indicates that the compound is a human MCH1 receptor antagonist, wherein the DNA encoding the human MCH1 receptor comprises the sequence shown in FIG. 1 (SEQ ID NO: 1) or contained in plasmid pEXJ.HR-TL231 (ATCC Accession No. 203197), the known human MCH1 receptor agonist is Melanin-concentrating hormone (MCH) or an analog of MCH, and the cells do not express the MCH1 receptor prior to transfecting them.

2. A process for determining whether a chemical compound specifically binds to and inhibits activation of a human Melanin-concentrating hormone 1 (MCH1) receptor, which comprises separately contacting cells expressing on their cell surface the human MCH1 receptor and capable of producing a second messenger response upon activation of the human MCH1 receptor, wherein such cells do not normally express the human MCH1 receptor and the DNA encoding the human MCH1 receptor comprises the sequence shown in FIG. 1 (SEQ ID NO: 1) or contained in plasmid pEXJ.HR-TL231 (ATCC Accession No. 203197), with both the chemical compound and a second chemical compound known to activate the human MCH1 receptor, and with only the second chemical compound, under conditions suitable for activation of the human MCH1 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the human MCH1 receptor, wherein the second chemical compound is Melanin-concentrating hormone (MCH) or an analog of MCH.

3. The process of claim 2, wherein the second messenger response comprises chloride channel activation and the change in second messenger response is a smaller increase in the level of inward chloride current in the presence of both the chemical compound and the second chemical compound than in the presence of only the second chemical compound.

4. A method of screening a plurality of chemical compounds not known to inhibit the activation of a human Melanin-concentrating hormone 1 (MCH1) receptor to identify a compound which inhibits the activation of the human MCH1 receptor, which comprises:

(a) contacting cells transfected with and expressing the human MCH1 receptor, wherein such cells do not normally express the human MCH1 receptor and the DNA encoding the human MCH1 receptor comprises the sequence shown in FIG. 1 (SEQ ID NO: 1) or contained in plasmid pEXJ.HR-TL231 (ATCC Accession No. 203197), with the plurality of compounds in the presence of a known human MCH1 receptor agonist, under conditions permitting activation of the human MCH1 receptor, wherein the known MCH1 receptor agonist is Melanin-concentrating hormone (MCH) or an analog of MCH;

(b) determining whether the activation of the human MCH1 receptor is reduced in the presence of the plurality of compounds, relative to the activation of the human MCH1 receptor in the absence of the plurality of compounds; and if so (c) separately determining the extent of inhibition of activation of the human MCH1 receptor for each compound included in the plurality of compounds, so as to thereby identify the compound which inhibits the activation of the human MCH1 receptor.

5. The process of any of claim 1, 2 or 4, wherein the cell is an insect cell.

6. The process of any of claims 1, 2 or 4, wherein the cell is a mammalian cell.

7. The process of any of claims 1, 2 or 4, wherein the cell is a mammalian cell which is nonneuronal in origin.

8. The process of any of claims 1, 2 or 4, wherein the cell is a COS-7 cell, a CHO cell, a 293 human embryonic kidney cell, a NIH-3T3 cell, a mouse Y1 cell, or a LM(tk-) cell.

* * * * *